United States Patent [19]
King et al.

[11] Patent Number: 5,528,155
[45] Date of Patent: Jun. 18, 1996

[54] SENSOR FOR MEASURING MATERIAL PROPERTIES

[75] Inventors: Edward K. King, Cambridge; Harry West, Arlington; Edward Bernardon, Bedford, all of Mass.

[73] Assignee: Massachusetts Institute of Technology, Cambridge, Mass.

[21] Appl. No.: 235,567

[22] Filed: Apr. 29, 1994

[51] Int. Cl.[6] .................................................. G01R 27/08
[52] U.S. Cl. .......................... 324/713; 156/64; 324/690
[58] Field of Search ..................................... 324/713, 715, 324/690, 724, 689, 667, 663; 156/64; 264/40.2; 422/62

[56] References Cited

U.S. PATENT DOCUMENTS

| 3,383,863 | 5/1968 | Berry . | |
|---|---|---|---|
| 3,791,792 | 2/1974 | Lindsay | 264/40.2 |
| 4,236,109 | 11/1980 | Ingle, Jr. | 324/690 |
| 4,399,100 | 9/1983 | Zsolnay et al. | 422/62 |
| 4,423,371 | 12/1983 | Senturia et al. . | |
| 4,510,103 | 4/1985 | Yamaguchi et al. | 262/40.2 |
| 4,777,431 | 10/1988 | Day et al. | 324/690 |
| 4,868,769 | 9/1989 | Persson | 264/40.1 |
| 5,208,544 | 5/1993 | McBrearty et al. | 324/690 |
| 5,210,499 | 5/1993 | Walsh | 324/690 |
| 5,219,498 | 6/1993 | Keller | 324/663 |

FOREIGN PATENT DOCUMENTS

| 0127958B1 | 3/1992 | European Pat. Off. . | |
|---|---|---|---|
| 1323982 | 7/1987 | U.S.S.R. | 324/724 |

OTHER PUBLICATIONS

Kranbuehl, D. E., "In–situ on–line measurement of composite cure with frequency dependent electromagnetic sensors", Plastics, Rubber and Composites Processing and Applications, vol. 16, Apr. 1991, 000–000.

Crabtree, D. J., "Ion Graphing as an In–Process Cure Monitoring Procedure for Composite and Adhesively Bonded Structures", 22nd National Symposium & Exhibit, SAMPE, vol. 22, 1977, pp. 636–649 (No month).

Micromet Instruments, Inc., "Leading–Edge Dielectric Analysis Systems for Cure Monitoring & Polymer Characterization, Automated Material QA/QC & SQC Testing, and Real Time Thermoset Molding Control".

Primary Examiner—Maura K. Regan
Attorney, Agent, or Firm—Fish & Richardson

[57] ABSTRACT

Sensors for measuring properties of resinous materials having an insulating member bonded directly to a conductive strand and a narrow thread-like geometry in which only a very small surface area of the connecting strand is exposed. The sensors provide advantages in the variety of environments in which measurements can be made, in the variety of types of measurements that can be made, and in the ease of constructing the sensors and in making the measurements.

40 Claims, 16 Drawing Sheets

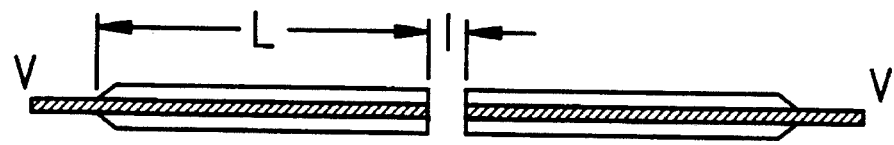
FIG. 4
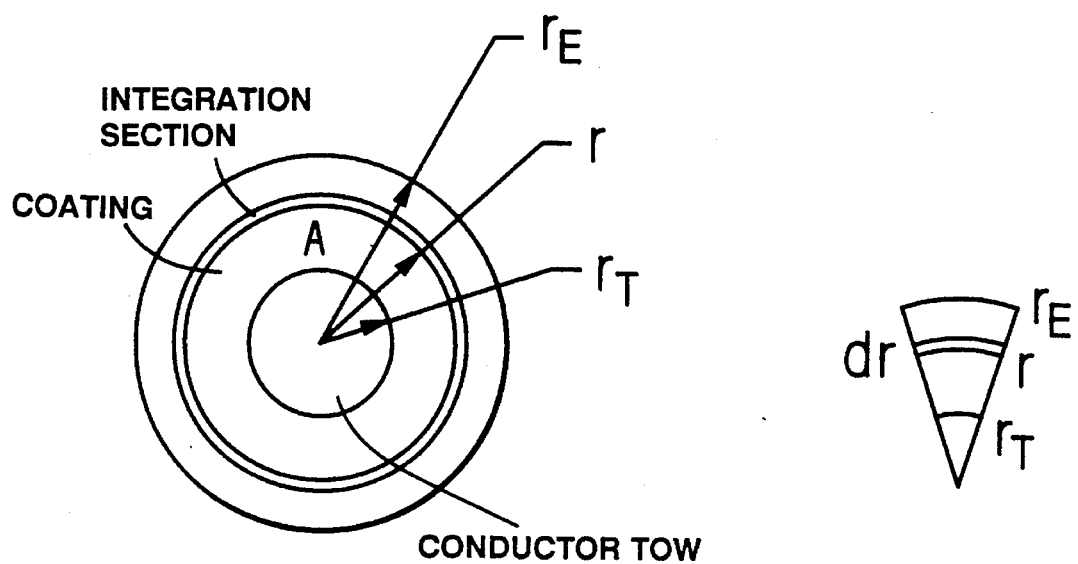
FIG. 4a
FIG. 4b

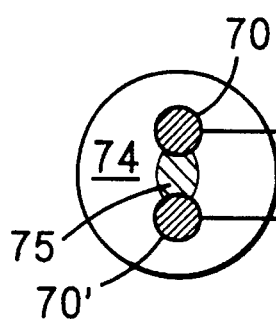
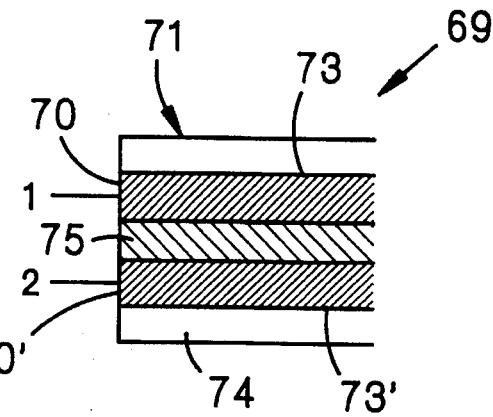
FIG. 10   FIG. 10a
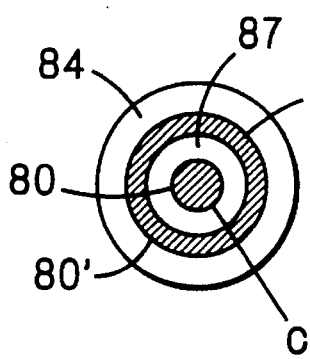
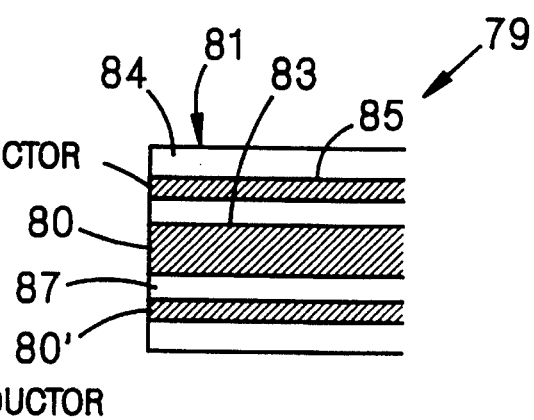
FIG. 11   FIG. 11a
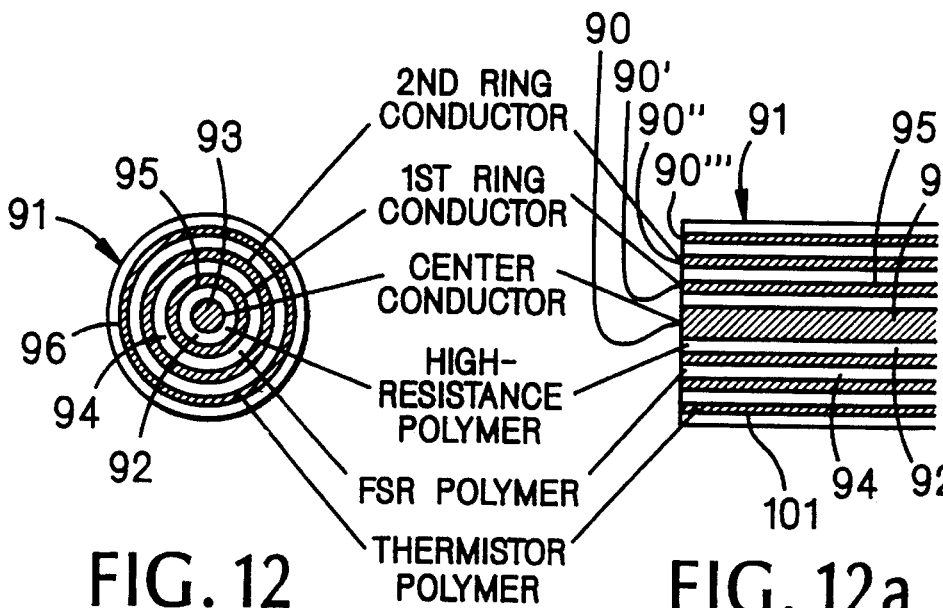
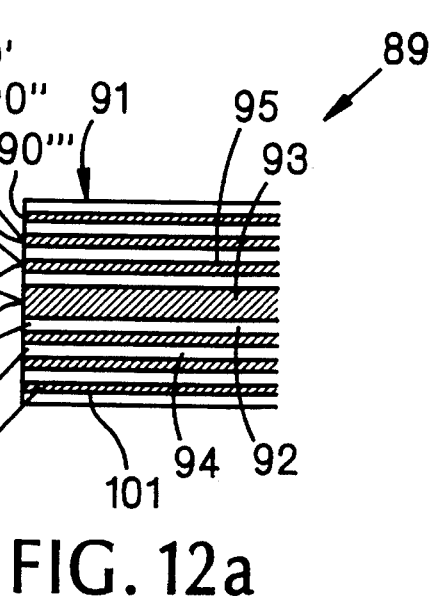
FIG. 12   FIG. 12a

SENSOR FOR MEASURING MATERIAL PROPERTIES

FIELD OF THE INVENTION

This invention relates to measuring properties of materials.

BACKGROUND OF THE INVENTION

Composite materials are made of axially strong, stiff reinforcing fibers that are embedded in a matrix of a tough resin. The fibers most widely used in composites are carbon, glass, aramid (Kevlar®), and boron. These fibers can be made into thin, flat ribbons or long narrow strands which can be weaved or stitched to form a reinforcing fabric.

The resins are typically thermosets or thermoplastics. Thermosets include, for example, epoxies, polyesters, and polyimides. Thermosets are cured at an elevated temperature and cannot be reshaped by reheating. Thermoplastics include, for example, styrene, acrylics, cellulosics, polyethylenes, vinyls, nylons, and fluorocarbons. Thermoplastics can be reshaped by raising them above their glass transition temperature. This property limits thermoplastics to use in lower temperature environments only.

Composite materials can exhibit high strength, resistance to creep, fatigue, and chemical attack. But improper curing can result in unreliable composite parts.

SUMMARY OF THE INVENTION

Sensors for measuring properties of resinous materials having an insulating coating bonded directly to a conductive strand and a narrow thread-like geometry in which only a very small surface area of the connecting strand is exposed. The sensors provide advantages in the variety of environments in which measurements can be made, in the variety of types of measurements that can be made, and in the ease of constructing the sensors and in making the measurements.

In a first aspect, the invention features a sensor for measuring the properties of a resinous material. The sensor includes a thread-like construction that can be placed in contact with the resinous material. The thread-like construction is composed of at least two electrically conductive strands having preformed insulating members over their lengths. The strands extend to ends that are spaced to form a sensing location where an electrical property can be measured by connecting the strands to sensor electronics that are located remotely from the resinous material.

Embodiments may include one or more of the following features. The ends of the strands are spaced and arranged to form an axial gap. The ends of the strands are exposed to the resin. The sensor is constructed for measuring the properties of a composite material composed of resin and conducting components. The ends of the strands being spaced a distance less than the width of the conducting components. The ends of the strands are spaced between about 0.01 to 2.25 inches. The strands have a diameter in the range of 100 μm to 2 mm. The sensor is constructed for measuring the properties of a composite material composed of resin and conducting reinforcing fibers, and the conductive strands being composed of the same substance as the reinforcing fibers. The conductive strands and the reinforcing fibers have comparable cross-sectional dimensions. The conductive strands and reinforcing fibers are composed of carbon fibers. The insulating member is a coating that bonds to the resinous material. The polymer coating is formed from a resin that is in a partially cured state prior to placing the sensor in contact with the resinous material and the resin forming the polymer coating being cured under conditions that cure the resin of the resinous material. The insulating polymer coating is formed from the same resin used in the resinous material. The insulating member incorporates a glass fiber sock and an insulating polymeric material. The space between the ends includes a substance with an electrical property that varies with the material property. The substance is a pressure-sensitive polymer with an electrical property that varies with pressure applied to the polymer.

In another aspect, the invention features a method for forming a cured resinous material, including providing an uncured resin and a mold, providing a thread-like construction composed of an electrically-conductive strand having an insulating member preformed over its length, forming a sensor by removing a portion of the thread-like construction at a desired location to create two sensor threads with ends at which the electrically conductive strands are exposed and spaced to form a sensing location therebetween, connecting the strands to sensor electronics, and curing the resinous material in the mold while monitoring electrical properties in the gap with the sensor electronics.

Embodiments may include one or more of the following features. The sensor is formed by hand-cutting the thread-like construction to form the gap after the thread-like construction has been placed in the mold. The gap is formed with a width in the range of about 0.01 to 2.25 inches. The gap is formed with a width in the range of about 0.01 to 0.25 inch.

In another aspect, the invention features a system for measuring the properties of a resinous material. The system includes a sensor that can be positioned in contact with the resinous material. The sensor has a thread-like construction that is composed of at least two electrically conductive strands having preformed insulating coatings and extending to sensing locations where an electrical property can be measured. Sensor electronics are connected to the strands for measuring the electrical property.

Embodiments may include one or more of the following features. A plurality of the sensors arranged with the sensing locations at desired positions across the resinous material, and sensor electronics are provided for monitoring the cure properties from the desired locations. The resinous material is a composite including a resin and conducting reinforcing fibers in a fabric or mat, and the thread-like construction is integrated in the reinforcing fabric or mat. The sensing locations include a gap where the ends of the conductive strands are axially opposed. The thread-like constructions are arranged in multiple layers forming a grid pattern and the sensing locations formed at overlapping regions of threads in different layers. The sensor and sensor electronics are constructed to measure the presence of resin at the sensing location. The sensor and sensor electronics are constructed to measure the degree of cure of the location of the sensor. The sensor and sensor electronics are constructed for measuring properties of the material after cure of the material.

In another aspect, the invention features an article of manufacture that is a cured composite of a resin and conducting reinforcing fibers, including embedded therein, a sensor having a thread-like construction composed of at least two carbon fibers with preformed insulating polymer coatings over their lengths. The carbon fibers are spaced to form a sensing location where an electrical property can be measured by connecting the sensor to sensor electronics located remotely from the composite material.

In another aspect, the invention features a sensor for measuring multiple properties of a resinous material, including a thread-like construction composed of at least two electrically conductive strands having a preformed insulating coating and, in a first sensing location, the strands being arranged to measure an electrical property that varies with a first material property, and, in a second sensing location, the strands being arranged to measure an electrical property that varies with another material property. The strands are constructed for connection to sensor electronics.

Embodiments of the invention include one or more of the following features. The conductive strands are arranged concentrically. The conductive strands are arranged in parallel. The conductive strands are arranged to be exposed to the composite material in the first sensing location for measuring a first material property and the conductive strands are arranged to be exposed to a polymeric substance with an electrical property that varies with second material property. The polymeric substance is selected from the group consisting of temperature-sensitive polymers and pressure sensitive polymers.

Further features and advantages follow.

BRIEF DESCRIPTION OF THE DRAWING

FIGS. 4–4b are schematics defining variables used in determining an insulating coating thickness for sensors according to the invention;

FIGS. 10–10a are schematic cross-sectional views, end-on and longitudinal, respectively, of another embodiment of a sensor according to the invention;

FIGS. 11–11a are schematic cross-sectional views, end-on and longitudinal, respectively, of another embodiment of a sensor according to the invention;

FIGS. 12–12a are schematic cross-sectional views, end-on and longitudinal, respectively, of another embodiment of a sensor according to the invention;

DESCRIPTION OF THE PREFERRED EMBODIMENTS

Figure 1:
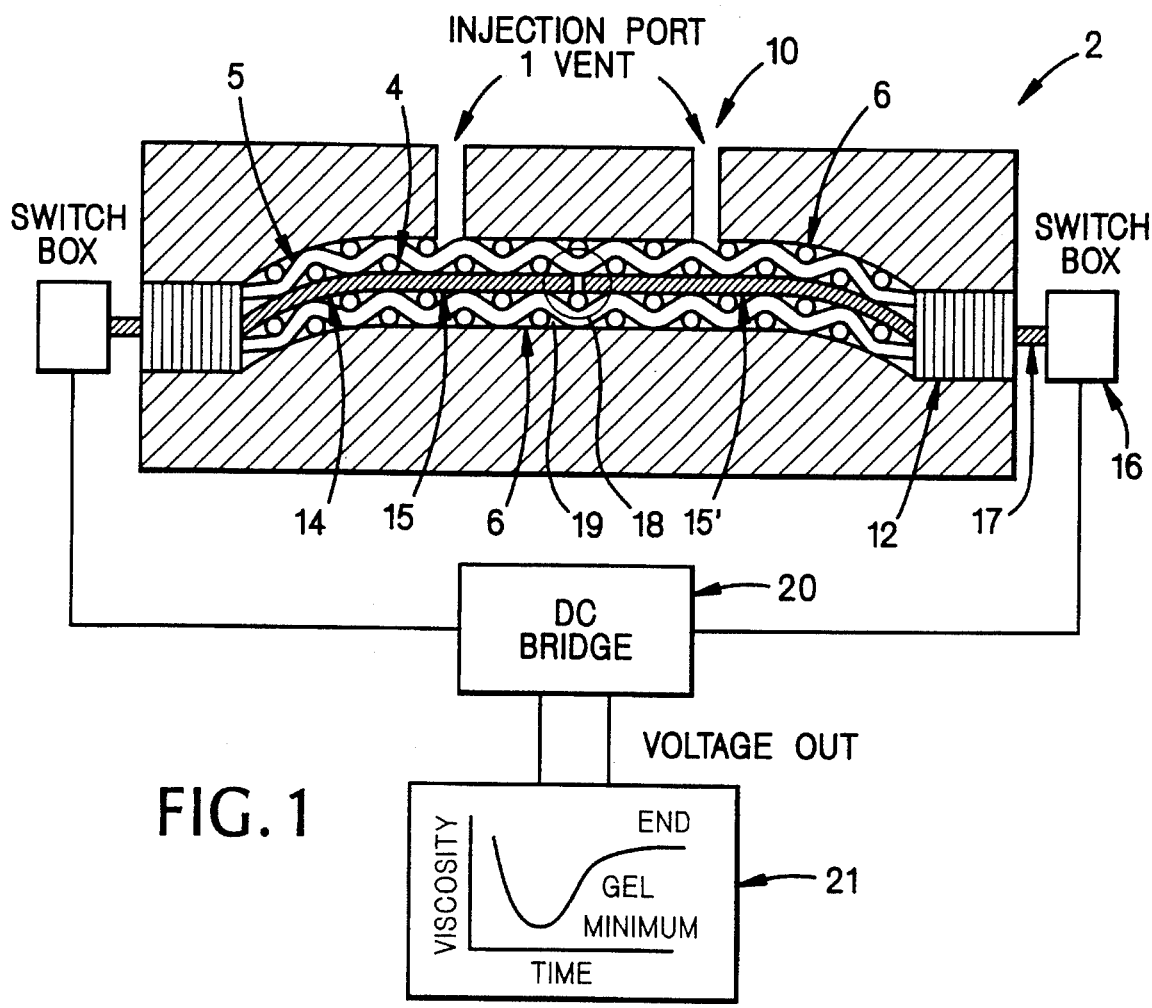
FIG. 1 is a schematic view, in partial cross-section, of a mold assembly including a sensor system according to the invention.

Referring to FIG. 1, a composite material is formed in a mold 2 by laying a prepregnated or dry woven reinforcing fabric 4 made, e.g., of woven carbon fibers 5, along the walls 6 of the mold. For a dry woven fabric, amorphous resin is injected through injection ports/vents 10. The mold is heated to cure the resin. The mold includes gaskets 12 at the edges to keep the resin from leaking out. In this example, the mold has a gentle curvature so the finished piece takes its shape, which might be suitable for use as a door for an automobile, for example.

A sensor 14 for monitoring the cure of the material is positioned in direct physical contact with the reinforcing fabric. As illustrated, the sensor 14 is formed of a pair of generally cylindrical, narrow, flexible threads 15, 15' that are arranged to form a gap 18 at a sensing location 19.

Figure 2:
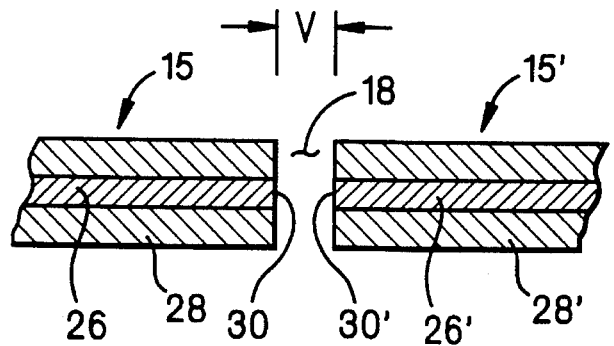
FIG. 2 is a greatly enlarged cross-sectional view of a portion of a sensor according to the invention.

Referring as well to FIG. 2, a greatly enlarged cross-sectional view of the sensing location, the threads are composed of a conducting strands, carbon fibers 26, 26', which have, over their length, polymer coatings 28, 28'. The polymer coatings 28, 28' insulate the conducting carbon fibers to prevent shorting between the fibers 26, 26' and other conducting elements in the mold, especially, for example, the carbon reinforcing fibers 5. The sensor gap 18, which is formed by removing a section of a single continuous polymer coated strand, exposes ends 30, 30' of the fiber 26, 26' so that an electrical resistance can be measured between the ends. The gap is kept small enough so that the conducting reinforcing fibers, or other conducting species in the resin, do not substantially enter the gap and make contact with the exposed ends of the sensor strands.

The sensor 14 has lead portions 17, 17' also including an insulating coating, which extend through the gasket 12 so the sensor can be connected to coupling electronics 16, which include a relay multiplexer (e.g. FIG. 11c) that allows multiple sensors to be monitored. The coupling electronics 16 are, in turn, connected to sensor electronics 20, including a DC bridge. Using the DC bridge, a resistance change or change in the complex dielectric constant in the gap 18 between the exposed ends 30, 30' is measured as a variation in voltage across a fixed resistor of the bridge. The signals are displayed by analysis electronics 21.

During curing, the resin enters the gap and the resistance of the resin varies. The signal can be analyzed to indicate the viscosity over time so that the cure cycle of the resin can be studied or monitored. A discussion of cure monitoring by DC resistance, a technique known as "ion graphing" is described in Crabtree "Ion Graphing as an In Process Cure Monitoring Procedure for Composite and Adhesively Bonded Structures", 22nd National Symposium and Exhibition, SAMPE, 22, 1977, p. 6—6.

Figure 3:
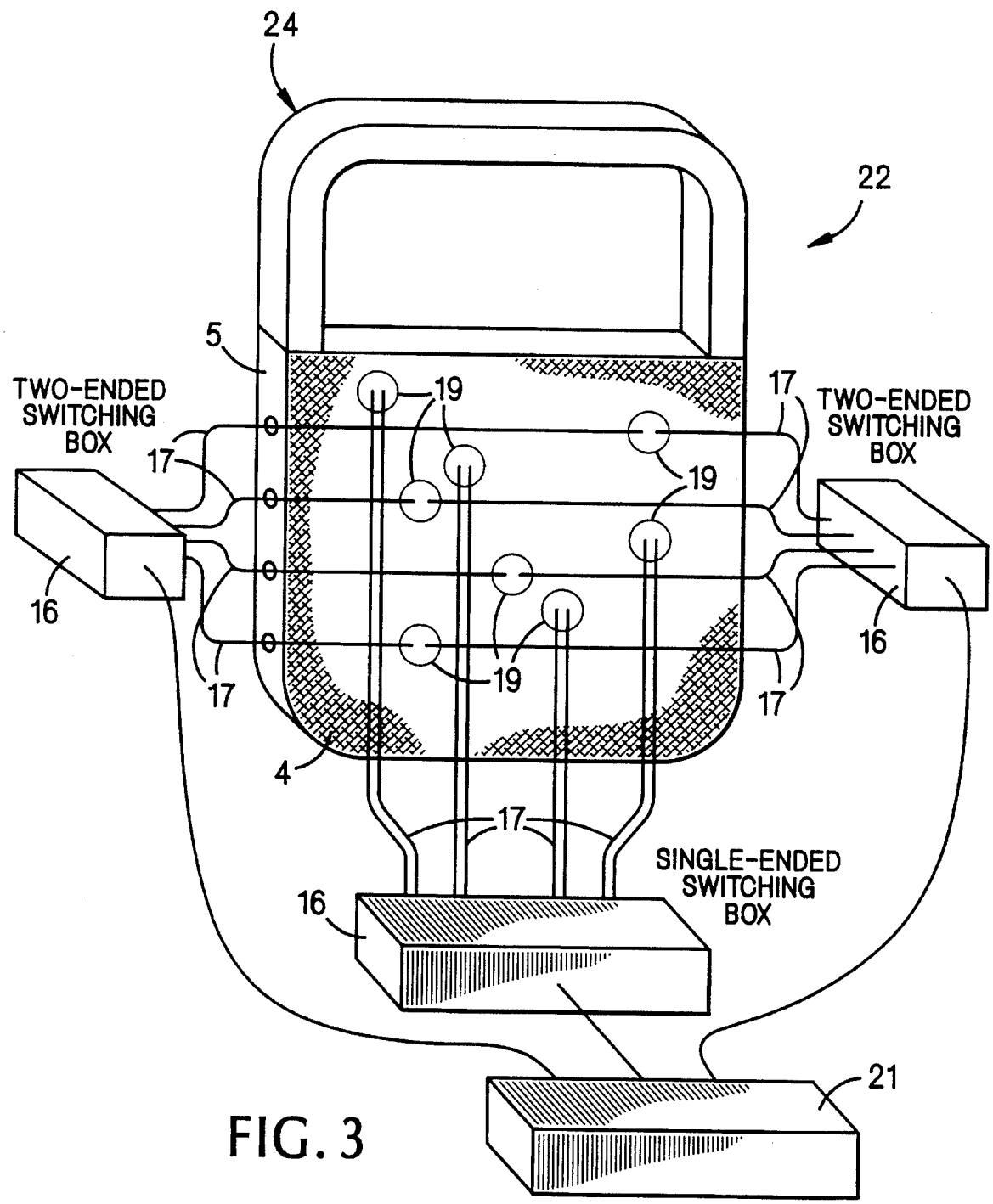
FIG. 3 is a schematic perspective view of a composite piece after curing with sensors according to the invention.

Referring as well to FIG. 3, after curing the resin, a solid, tough composite piece 22 composed of the reinforcing fabric 4 (phantom) embedded within the cured resin matrix, can be removed from the mold. Additional pieces 24, made of composite or other materials (which may also include sensors, not shown), can be attached to the composite piece 22 to form a useful part, e.g., the door to an automobile. Sensors 14 remain embedded in the resin. (As made clear in this perspective view, multiple sensors are provided across the mold and the piece so that sensing can take place at multiple sensing locations 19.) After curing, the lead portions 17, 17' can be removed and the piece put to use.

The sensors, because of their construction, an insulating coating bonded directly to the conducting strand, and geometry, a narrow thread in which only a very small surface area of the connecting strand is exposed, provide advantages in the variety of environments in which measurements can be made, in the variety of types of measurements that can be made, and in the ease of constructing the sensors and in making the measurements.

The sensors can be used in composite environments that include conducting components, such as carbon reinforcing fabrics, because the conducting strands on the interior of the sensor threads are insulated and protected by the exterior insulating coating. The sensor thread can directly contact the reinforcing fabric without shorting. The small surface area of the conducting thread that is exposed is also protected by the coating in that the coating acts as a stand-off that separates the exposed portion from the reinforcing fabric. For example, as illustrated above, the exposed portion of the conducting strand is preferably at the end of the thread, axially flush with the end of the insulating coating. The ends of the sensor threads are preferably arranged to form an axial gap which may be sufficiently short that conducting components, e.g. reinforcing fibers, cannot fit into the gap. This sensor geometry thus effectively presents a barrier that prevents conducting components from entering the gap, while allowing the fluid resin to enter so that measurements can be made.

The sensors are also simple to make and use. Another feature of the sensor is that the electrical path in the gap between the small exposed portions of conducting strands is a substantially non-ohmic in typical embodiments. Thus, the shape of the DC signals produced during cure are largely independent of small changes in the length (L) of the gap. This property is believed to be due to electrical phenomena present when there are a very small number of charge carriers in a material, such as in the case of a resin, having a resistance in the range typically from 1 megaohm to 1 gigaohm. The gap length is typically in the range of about 0.01 to 2.25 inch.

This feature provides the advantage of permitting the sensors to be constructed cheaply and easily. For example, the sensors can be conveniently constructed by hand-cutting gaps in continuous threads just prior to the curing operation and without great attention to precision. The gaps are typically formed with gap length in the range of about 0.01 to 0.25 inch. However, the sensors can also be used in environments where the gap length is likely to change over time for example to a length of around 2 inch, such as during forming, during curing when the resin flows across the sensor, and in the finished piece as it is bent under stress, as will be discussed below.

The geometry and construction of the sensors enables embodiments in which the sensors need not be removed from the composite after curing because they do not affect the performance of the composite piece. The conducting strand may be a carbon fiber of the same or comparable tow size, stiffness, thermal characteristics, etc. as the reinforcing fibers and the insulating coating may be compatible with the resin of the composite. Since the sensors need not be removed, they can be used to make measurements after curing, that are characteristic of the finished composite piece.

The sensors can also be used to make a wide variety of measurements. After cure, embodiments of the sensors can be connected to different sensor electronics for analysis of properties, such as temperature or mechanical properties like stress and strain. Multiple properties may be measured using the same sensor threads.

Many advantages can be gained from the small sizes that can be obtained with the sensors. For example, the sensors can be made thin and flexible so that they can be placed in small composite parts with complex shapes. The sensor threads typically have an overall diameter typically in the range of 1 mm to 10 mm, the conducting strands have a diameter in the range of 2 mm to 100 μ microns, and the small exposed portions of the strands, typically corresponding to the end of the strands, is in the range of 3.0 to 0.008 mm$^2$. The signal strength from the sensors may be in the range of a few milliamps to less than a nanoamp, e.g., down to 100 picoamps.

Conducting Strand Selection

Various types of conducting strands can be used. For example, suitable materials include carbon fiber, graphite, aluminum wire, copper wire, lead-coated glass, electrically conductive polymers, powdered metal coated materials or other organic or inorganic conductive materials. Carbon fibers are particularly preferred. They are available in the form of a tow which is made up of fine carbon filaments (e.g. thousands) loosely bundled together with a slight twist. The fiber tows typically have diameters ranging from 100 μm to 2 millimeters. For sensors that are to be embedded in a composite piece, the tow size of the conducting strand is preferably comparable to the tow size of the reinforcing fibers so that the mechanical properties of the finished composite piece will not be substantially effected by the presence of the sensor strand.

In general, the strands can be selected based on size, mechanical, and thermal characteristics. In embodiments, the strand can be selected to enhance the performance of a composite piece. For example, a large diameter or stiff strand may be selected to add stiffness to the piece.

Insulator Selection

Various insulators can be used. Polymer coatings are preferred. The polymer is selected to be compatible with the properties of the resin used in the composite properties considered in selecting the polymer coating include:

(1) High and stable electrical resistivity, for example, of the same order as the resin or higher and preferably as determined by the calculations discussed below;

(2) High operating temperature and pressure; when the sensor is to be used in a thermoset resin and under high pressure forming processes, the polymer coating is desired, to be mechanically and electrically stable at temperatures, e.g., as high as 200° C. and pressures as high as 100 psi. In non-thermoset applications, temperature and pressure requirements to the insulator are determined based on reporting of the application.

(3) Flexible curing characteristics; for high compliance of the sensor within a composite material, the coating should remain somewhat soft and flexible after it has been cured.

(4) Bonding characteristics; in order for the electrode to be nonintrusive, the coating should bond well to both the resin and conductive strand.

(5) The thermal properties of the polymer are similar to the resin (e.g., coefficient of thermal expansion, coefficient of thermal conductivity);

(6) The polymer coating cures to a robust state; the polymer coating facilitates handling, reduces scrap, and adds toughness to the cured piece.

The polymer coating may be formed from the resin used in the composite. The resin may be partially cured on the fiber prior to placing the fiber into the mold, and then cure completed along with the composite. Some thermoset resins can be "B-staged" into a rubbery state and although the B-staged resin may soften during the cure cycle of the composite material, it has consistently higher viscosity and electrical resistance than stock resins used in composite materials. An example of a liquid-form resin that can be B-staged to a rubbery state and then fully cured to a harder plastic are TACTIX resins (available from Dow Plastics, Midland, Mich.).

In some applications, it may be desirable to select a coating that does not bond firmly to the composite resin so that the sensor may be reused by simply stripping it from a composite material after measurements have been made. The coating may also include a pigment to visually indicate their location when woven into a reinforcing fabric.

In general, if the sensor is to be embedded in the composite piece, the insulator is selected so that the performance of the composite piece is not degraded by the presence of the sensor. A performance property of the composite piece can also be enhanced. For example, stiffness can be enhanced by providing a metal tube sheath around the conducting strand. A ceramic insulator can also be provided to form a stiff, tough sensor.

In various embodiments, an insulator sock can be made from nonconductive fibers such as glass which are braided or straight. The sock can be bonded (mechanically or by adhesive) or stitched to the conductive strand, slipped loosely over them, or integrally braided with the strand. The sock may be made by two or three dimensional braiding techniques. Glass fiber is bondable to most composite resins.

The insulator can also be formed of several of different materials to improve performance characteristics such as increasing insulation over the length of the strand to reduce leakage current and to improve bondability to a particular resin. For example, a glass fiber sock can be provided around the carbon filament and polymer coating provided over the glass fiber sock. In another example, the glass fiber sock is sandwiched between layers of polymer coatings. In another example, a glass fiber sock is provided over the strand and insulating polymer is provided in the interstitial spaces between the glass fibers, the sock thus acting as a matrix that holds the polymer.

Construction

Referring to FIGS. 4–4b, the coating thickness of the polymer preformed over a strand, e.g. a carbon fiber, can be determined based on a desired signal to noise ratio characteristic and the following system parameters:

$r_T$, conductor tow radius (A carbon fiber tow does not have to have a circular cross section, but may be assumed to simplify these calculations.)

L, length of electrode in the laminae;

l, gap length or sensor spacing;

$r_E$, electrode radius;

A, area of cylindrical integration section;

dr, thickness of cylindrical integration section;

r, distance to integration section;

In the derivation, the following variables are also defined:

$t=r_E-r_T$, coating thickness; $\Delta V=V_H-V_L$, potential difference between high and low potentials;

$\rho_R$, highest electrical resistivity of resin;

$\rho_c$, lowest electrical resistivity of coating material; and

N, desire signal to noise ratio;

$R_R$, resistance of resin; and $R_c$, resistance of coating material

In order to achieve the desired signal to noise ratio N, the current passing through the rod-shaped resin segment between the electrodes must be N times as large as the current leaking through the cylindrical coating. In other words, $i_{resin}$ and $i_{coating}$ must satisfy $$i_{resin} < N i_{coating} \qquad (1)$$

Assuming one electrode is at the high potential $V_H$, the other electrode and the resin outside of the sensing area are at the low potential $V_L$, then these currents can be expressed in terms of the potential difference and the corresponding resistances as:

$$i_{resin} = \frac{\Delta V}{R_R} \qquad (2)$$

$$i_{coating} = \frac{\Delta V}{R_C} \qquad (3)$$

Ignoring any fringe field and assuming the field between the electrodes has the same circular cross-section as the conductor, then the resistance of resin can be calculated using equation (4):

$$R_R = \frac{\rho_R l}{\pi r_T^2} \qquad (4)$$

The resistance of the coating material is calculated using equation (5) integrated over a series of cylindrical shells as shown in FIG. 10b.

$$R_C = \int_{r_T}^{r_E} \frac{\rho_C}{A} \, dr = \int_{r_T}^{r_E} \frac{\rho_C}{2\pi rL} \, dr = \frac{\rho_C}{2\pi L} \ln\left(\frac{r_E}{r_T}\right) \qquad (5)$$

Now, substituting the definition of coating thickness $t=r_E-r_T$ into Equation (5) provides the following.

$$R_C = \frac{\rho_C}{2\pi L} \ln\left(1 + \frac{t}{r_T}\right) \qquad (6)$$

Solving Equation (1) the minimum coating thickness is:

$$t_{min} = r_T \exp\left[2N\left(\frac{L1}{r_T^2}\right)\left(\frac{\rho_R}{\rho_C}\right)\right] - r_T \qquad (7)$$

As discussed above, the gap between the threads is preferably as small as possible (e.g. between about 0.01 to 2.25 inch, over which the resistance is largely independent of the length). The gap length and orientation is also selected based on the thickness of the insulating coating and the size of the conducting components in the composite. A thicker insulating coating generally acts as a better stand-off allowing larger gap lengths to be used. A smaller gap length, particularly in axial gap arrangements, presents a more effective barrier to conducting components. Typically, in axial gap arrangements, the gap length is equal to or less than the diameter of conducting reinforcing fibers used in the composite. For example, the gap length may be in the range of about 0.01 to 0.25 inch. In other arrangements, rather than an axial gap between opposed ends of the threads, the threads are parallel and the ends of the threads are in a side-by-side arrangement. (See the sensors extending from the bottom of the composite piece in FIG. 3). In other embodiments, two conductive strands are provided in a parallel or concentric arrangement in a single thread. The strands are separated by an insulating material and extend to ends which are exposed and adjacent one another at the end of the thread. In other arrangements, rather than measuring between the ends, the threads are arranged to overlap at portions along their lengths and the measurement is made between the overlapping portions.

Sensing Arrangements

The number and location of the sensor threads and sensing locations can be optimized for a particular application. As illustrated above, in embodiments, a pair of threads may be used to provide a single sensing location or a number of threads may be used to provide a uniform series of sensing locations across a desired portion of a composite piece.

Figure 5:
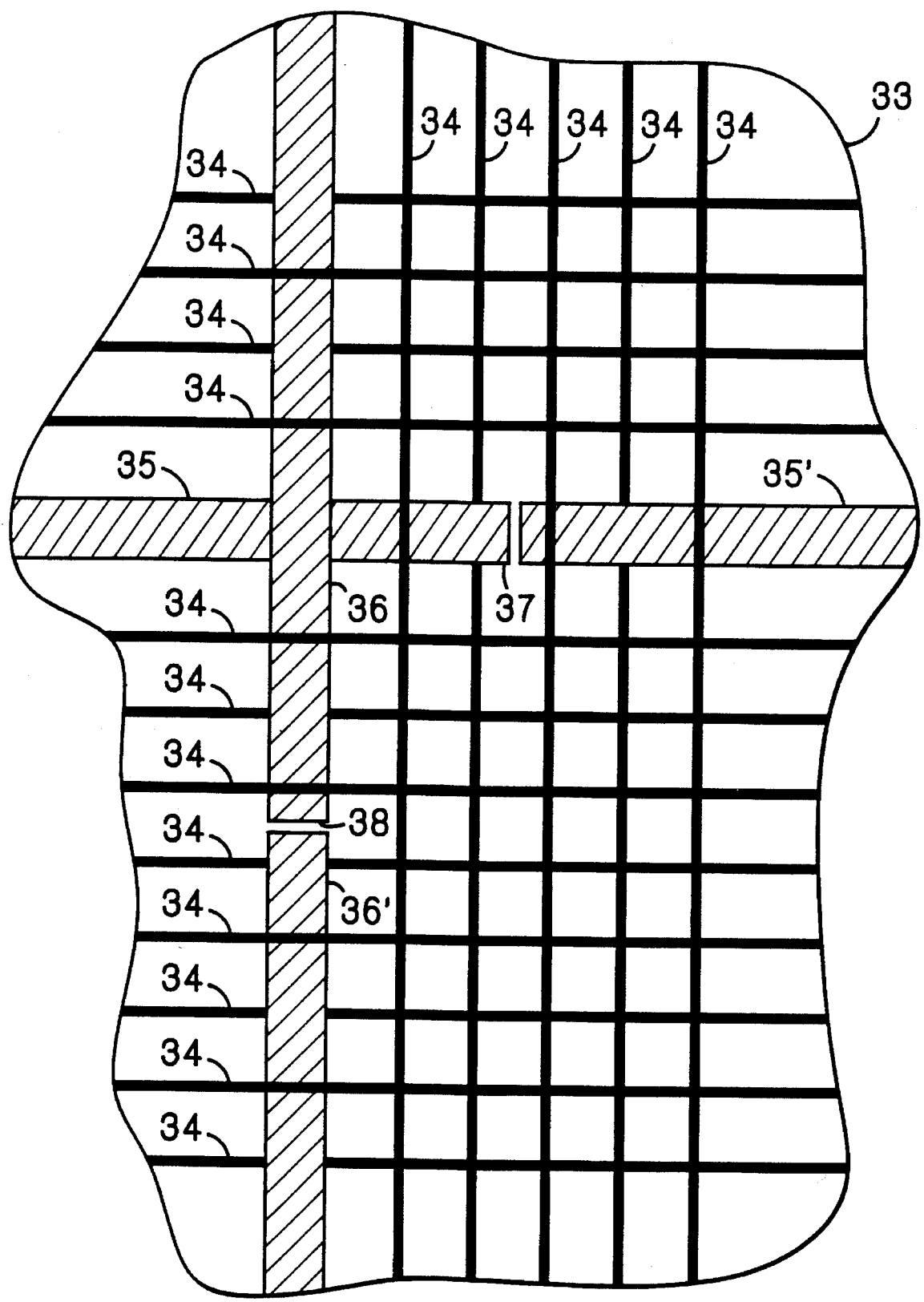
FIG. 5 is a schematic of a reinforcing fabric including sensors integrated within the fabric weave, according to the invention.

Referring to FIG. 5, in embodiments, the sensor threads can be woven into a reinforcing fabric. The fabric 33 is formed by co-weaving a series of reinforcing fibers 34, such as carbon fibers, and sensor threads. Gaps 37, 38 are created at desired locations in the fabric during layup to create sensing locations between the ends of sensor thread pairs 35, 35', 36, 36'. Since the sensor threads include an insulating coating, they can be woven with and be in direct contact with the conducting reinforcing fibers 34. Alternatively, the fabric can be woven entirely from sensor threads and sensor locations created at desired (e.g. randomly selected) locations.

Figure 6:
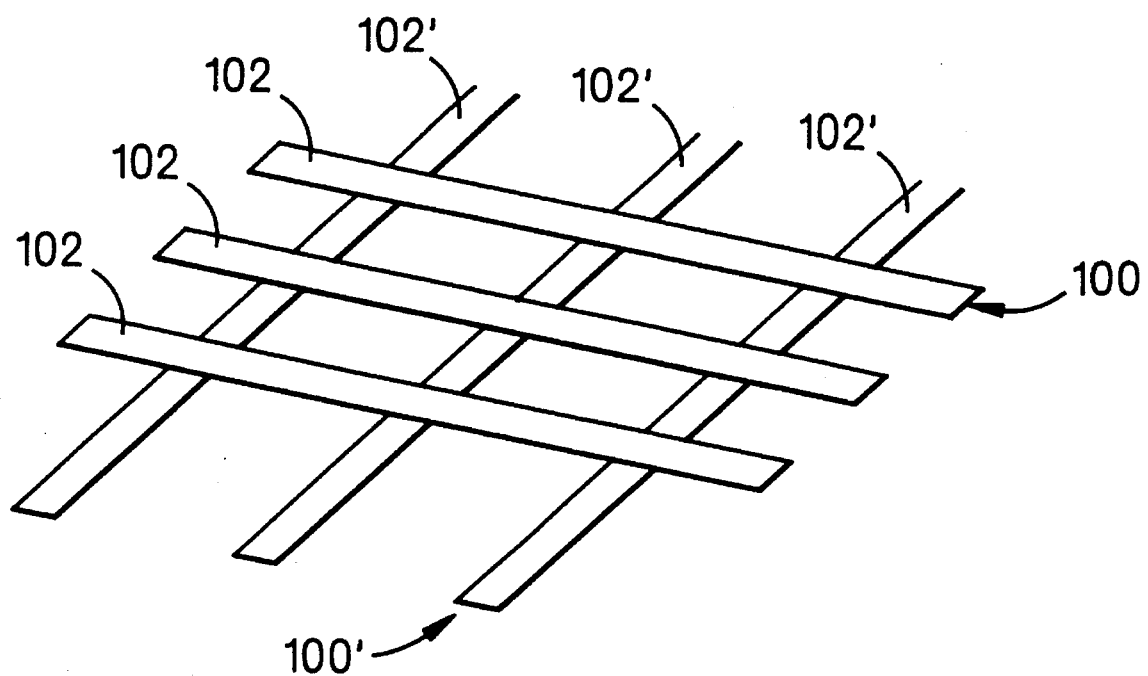
FIG. 6–6a are schematic perspective and cross-sectional side views of a sensor arrangement according to the invention including an overlapping grid.
Figure 6A:
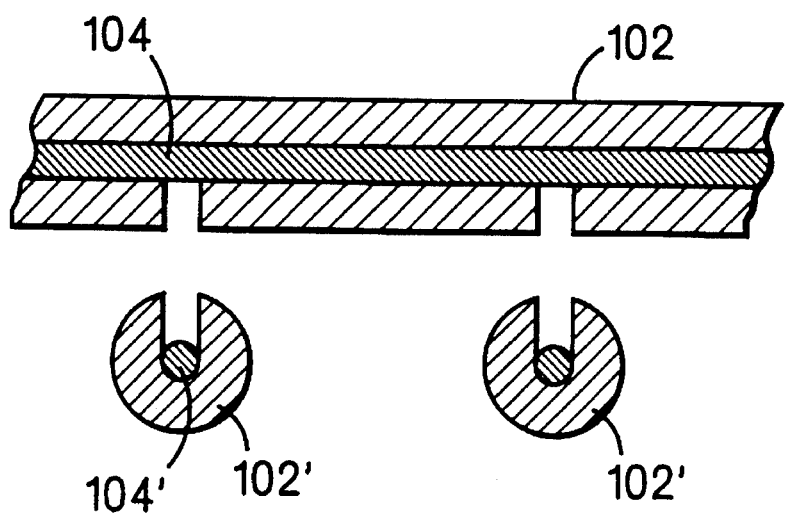

Referring to FIGS. 6 and 6a, in other arrangements, multiple layers 100, 100' of threads 102, 102' can be placed in the mold to form a grid, sandwiching resin between them. The polymer coating can be removed from the sensor threads at overlapping regions in different layers to expose the conducting strands 104, 104' and the measurement made between the layers. The area of the fiber that is exposed is, again, kept small to create a narrow opening into which conducting components of the resin will not fit. The insulator coating is preferably relatively thick. In embodiments such as this, the number of sensing locations may be greater than the number of sensor threads. A grid system is discussed in Walsh U.S. Pat. No. 5,210,499, the entire contents of which is incorporated herein by reference.

Sensors can be constructed so that they can be embedded in the composite part after curing, as discussed above, or, alternatively, the threads can be provided on the mold tool. The sensors may be attached to the floor of the tool so the threads and sensing locations are in direct contact with the resin during curing. The floor of the tool may also be provided with channels so the threads are recessed and do not become embedded in the cured piece.

In other embodiments, the threads can be embedded and later stripped from the composite piece after curing so the threads can be reused. In these latter embodiments, the threads are preferably provided with an insulating polymer coating that does not firmly bond to the resin used in the composite.

Sensing Temperature and Pressure

In embodiments, the sensor is constructed to indirectly measure composite material properties. For example, the sensor may be constructed to provide temperature measurements by using a thermistor polymer material as a coating on a portion of the carbon fiber. Thermistor materials have a large temperature coefficient, i.e., when the temperature changes, resistance changes substantially. Suitable thermistor-type polymers are available from Siemens Components, Inc., Iselin, N.J. and KCK America Inc., Mitsubishi Materials Corp., Rolling Meadows, Ill. Pressure measurements, which can be related to stress and strain of a material, can be made by using polymers that are force-sensitive resistor materials. Force-sensitive resistor materials, such as those available from Interlink, Carptenteria, Calif. and Advanced Composites Technology, Boston, Mass., have a large resistance variation under load.

Figure 7:
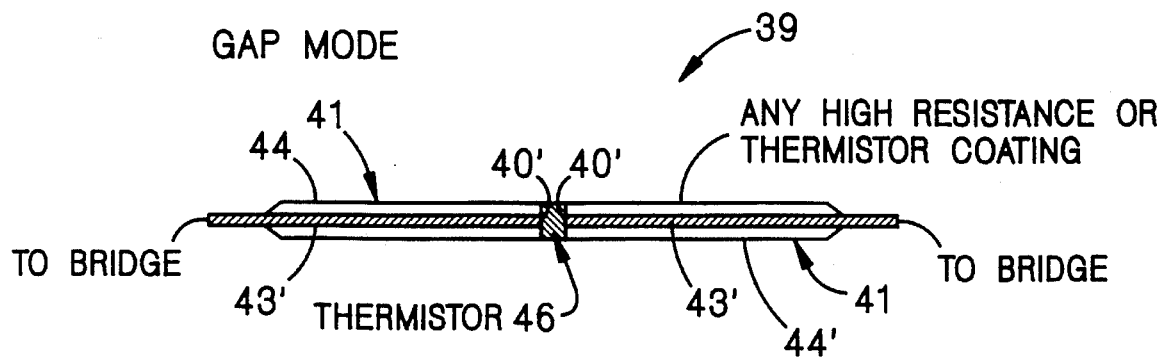
FIG. 7 is a schematic cross-sectional view of another embodiment of a sensor according to the invention.

Referring to FIG. 7, in an embodiment, the sensor 39 includes a pair of threads 41, 41' composed of carbon fibers 43, 43' with a high resistance coating 44, 44' and arranged with axially opposed ends 40, 40'. The gap between the ends is filled with a polymer 46 that is sensitive to temperature or pressure. A change in temperature or load in the part of the composite adjacent the polymer 46 will induce a variation in the temperature or load on the polymer 46, which can be detected as a variation in resistance between the ends 40, 40' of the fibers 43, 43'.

Figure 8:
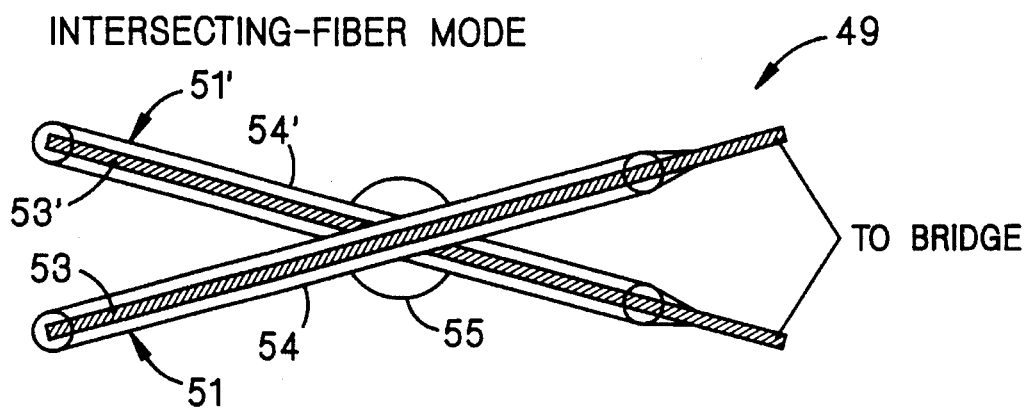
FIG. 8 is a schematic cross-sectional view of another embodiment of a sensor according to the invention.

Referring to FIG. 8, in another embodiment the sensor 49 includes a pair of threads 51, 51' composed of carbon fibers 53, 53' with coatings 54, 54' of a desired property-sensitive material (e.g., temperature or pressure). The threads are arranged so that there is a region of overlap 55. A resistance change measured between the two threads at the overlap 55 indicates the temperature or pressure variations in the adjacent portions of the composite. In the overlap, the strands may be in direct contact with each other or they may be separated by resin and reinforcing fiber.

Figure 9:
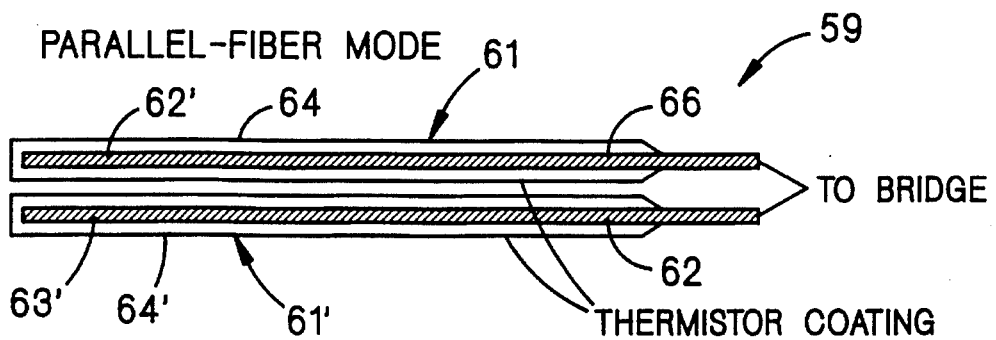
FIG. 9 is a schematic cross-sectional view of another embodiment of a sensor according to the invention.

Referring to FIG. 9, in another embodiment, the sensor 59 includes a pair of threads 61, 61' composed of fibers 63, 63' with coatings 64, 64' of a desired property-sensitive material. The threads are arranged in parallel. The resistance change measured between the two is a function of the average temperature or pressure variation over the length, thus providing a bulk measurement. The strands may be in direct contact or separated.

Sensing Multiple Properties

In still other embodiments, sensors are constructed so that several different properties may be measured. Referring to FIGS. 10 and 10a, in one embodiment, the sensor 69 includes a single thread 71 composed of a pair of fibers 73, 73' arranged in parallel with exposed ends 70, 70' an insulating polymer coating 74 on the outside of the fibers and a property-sensitive material 75 between the fibers. In this arrangement, direct sensing of the resin curing can be performed between the exposed ends of the fibers and indirect sensing of pressure and temperature can be performed by measuring electrical resistance between the two filaments at the location of the property-sensitive material 75. In a further embodiment, ends may be covered with polymer coating if only indirect measurements are desired. In a further embodiment, the property-sensitive material is replaced with a high resistance polymer and only direct measurements are made from the exposed ends 70, 70'. In still other embodiments, property-sensitive materials can be provided between the fibers at multiple locations along the axial length of the thread.

Referring to FIGS. 11 and 11a, in another embodiment, the sensor 79 includes a single thread 81 pair of conducting fibers 83, 85, arranged coaxially with exposed ends 80, 80' an insulating coating 84 on the outside of fiber 85, and a property-sensitive material 87 between the fibers.

Referring to FIGS. 12 and 12a, in another embodiment, the sensor 89 includes a thread 91 series of coaxially arranged fibers 93, 95, 97, 99 with exposed ends 90, 90', 90", 90''' insulating coatings 96, 101 on the outside of fiber 99, and between fibers 97, 99, respectively and property-sensitive materials 92, 94 between fiber 93 and fiber 95, and between fiber 95 and fiber 97, respectively. This embodiment may be arranged for measuring cure, temperature, and force. For example, cure measurements can be made between the ends 90" and 90''' of the fiber 97 and outermost annular fiber 99. Temperature measurement can be made between the fibers 93, 95 by providing a thermistor polymer for material 92. Force measurements can be made between 95 and 97 by providing material 94 as a force-sensitive polymer.

Uses

The sensors can be used in many different types of mold processes including, for example, resin transfer molding, flexible resin transfer molding, vacuum bagging, and others. The mold gasket may be formed as a series of thin metal tubes that are embedded in rubber. On the inside of the mold, the tubes reach the edge of the fabric at the location of the sensors. On the outside, the tubes are crimped onto wires which lead to sensor electronics. The openings of the tubes are sealed with a silicon RTV polymer.

Various sensor electronics can be used to monitor the cure of the composite. As discussed above, a preferred mode for monitoring resin cure is to measure ion conductivity using DC electronics. In other embodiments, AC ion conductivity, as discussed in Kranbuehl, "In-situ On-line Measurement of Composite Core with Frequency Dependent Electromagnetic Sensors", *Plastics, Rubber and Composites Processing and Applications*, 16 (1991) 000—000 (000—000?) may be used to monitor the cure of the composite. The sensors can also be used to make Van der Paw measurements, as discussed in L. J. Van der Paw, "A Method of Measuring Specific Resistivity and Hall Effect of Discs of Arbitrary Shape", *Philips Research Reports*, Vol. 13, No. 1, Februnary 1958, p. 1–9. The sensors can also be used to monitor the properties of materials other than composites. For example, the sensors can be used to make measurements in polymeric materials that do not have reinforcing fibers.

Other properties can be measured. For example, the sensor can be constructed, as noted above, to be sensitive to variations in pressure or temperature. These properties can be measured by connecting the sensors to the appropriate sensor electronics. As discussed, the sensors can be used to measure or monitor properties of the finished composite piece. Applications of this operational mode include ballistic damage assessment in armored vehicles, wind loading monitoring for airplane wings and helicopter blades, and fuel tank integrity monitoring for various vehicles. In embodiments, continuous threads can be embedded within the composite part and resistance variations caused by severing the thread by, e.g. a ballistic impact, can be monitored as an indication of ballistic damage.

EXAMPLE

Sensor Construction

In the experiments in this example, the carbon tow size was 1K (1,000 filaments) (Part No. 1KHTA-TW, available from BASF Structural Materials, Inc., Charlotte, N.C.). The carbon fiber tow is pre-coated with an insulating polymer prior to use.

In this sensor arrangement the sensor includes the following characteristics: $r_T=113$ µm, $L=30$ mm, $l=10$ mm, $\rho_R=10^8$ Ωcm, and $\rho_c=10^{15}$ Ωcm, which provides a minimum coating thickness for a desired S/N ratio of 100 of $t=70$ µm.

Silicon rubber (Slygard 567, a primerless silicon, available from Dow Corning, Midland, Mich.) was selected for coating the carbon fiber in this embodiment. The silicon is supplied in two parts, one part beige and one part black. The mixture ratio is 1:1 by volume and the mixture has a shelf life of 4 days at room temperature. The viscosity of the mixture at 5° C. is 13 poise, which increases if the mixture is left out at room temperature. The cure is carried out at 150° C. for two hours. Better adhesion of the polymer to the carbon fiber is obtained using a mixture that has been left at room temperature for at least two days.

The tow can be coated by dipping it into a flat dish filled with the liquid polymer silicon rubber so that substantially the entire length of the tow is immersed. The tow is removed from the dish and hung vertically from one of its ends. Excess polymer is then stripped off of the tow. The end by which the tow was hanging from is not coated and is sandwiched between two pieces of copper tape. The copper tape is used as an electrical contact to the sensor electronics. For freshly mixed silicon, a one-dip coat is about 7 µm, thus ten dips are required to make a sensor with the desired signal to noise ratio, as discussed above.

Electronics

Figure 13:
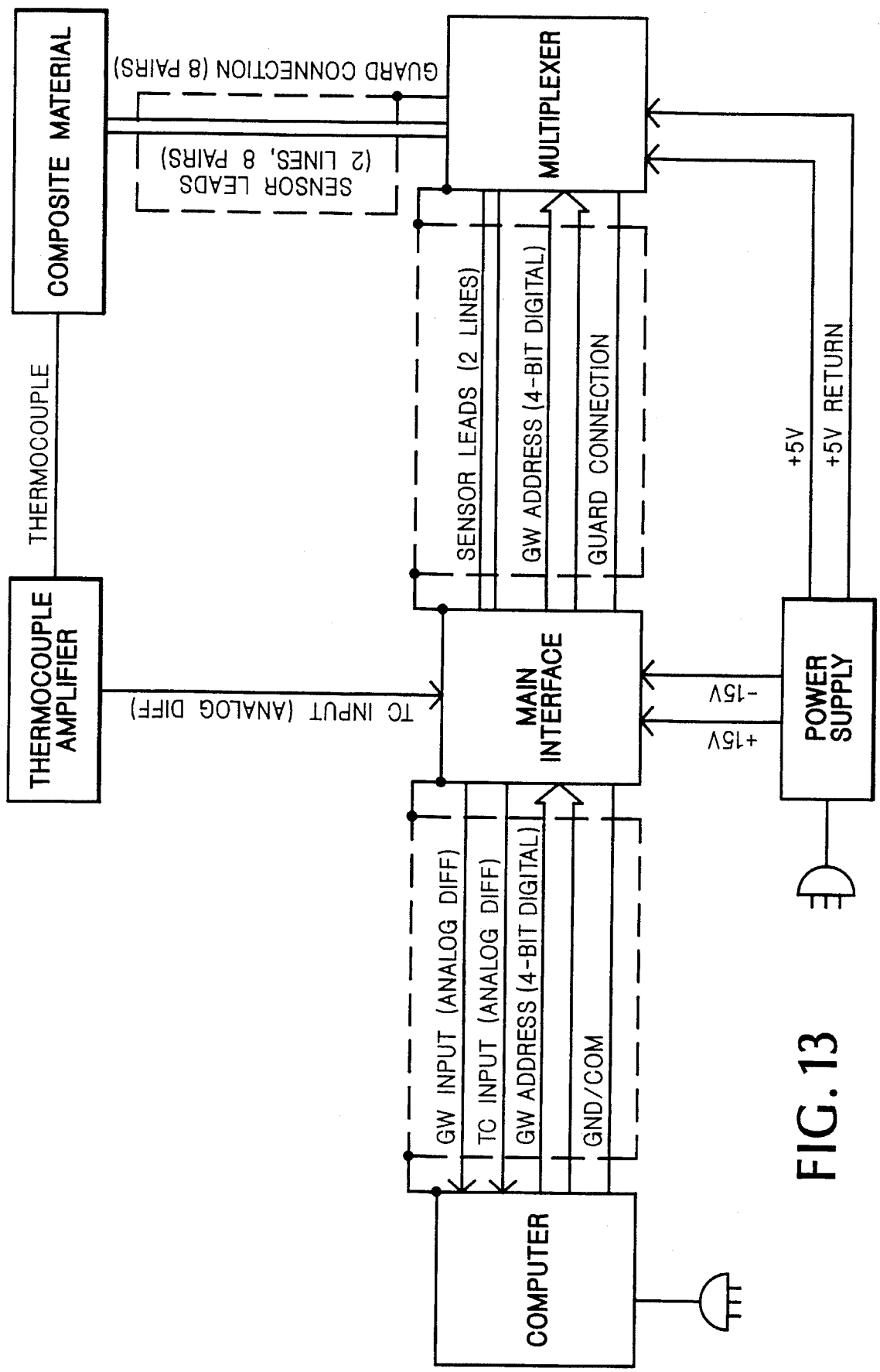
FIGS. 13–13e are circuit diagrams illustrating a sensor electronics arrangement.

Referring to FIG. 13, the electronics used to operate the sensor system has four major components: the computer, the analog to digital (A/D) converter, the Main Interface Unit (MIU), and the Multiplexer Unit. The computer, for example, an IBM 80286 compatible, is used to collect data, control the hardware, and provide the interactive user interface. The data acquisition board is a MetraByte DAS16 (MetraByte Asyst., Inc., Taunton, Mass.) which houses a 12-bit analog to digital (A/D) converter with 8 channels of differential or 16 channels of single-ended analog input, with adjustable gain. The data acquisition board also offers two 12-bit digital to analog outputs, a 4-bit digital input and a 4 bit digital output. The board is operated in 8-channel differential mode for increased noise rejection. The gain is set to yield a 0 to 10 volts span. With this setup, the resolution, or the least significant bit (LSB) was 2.44 mV with an accuracy of 0.01% ±1LSB. The control software used for the setup is Labtech Notebook a product of Laboratory Technologies Corp., Wilmington, Mass. Because the cure cycle used was 2 hours long the time between viscosity minimum and gelation was about 30 minutes. The sampling time was set at 30 seconds.

Figure 13A:
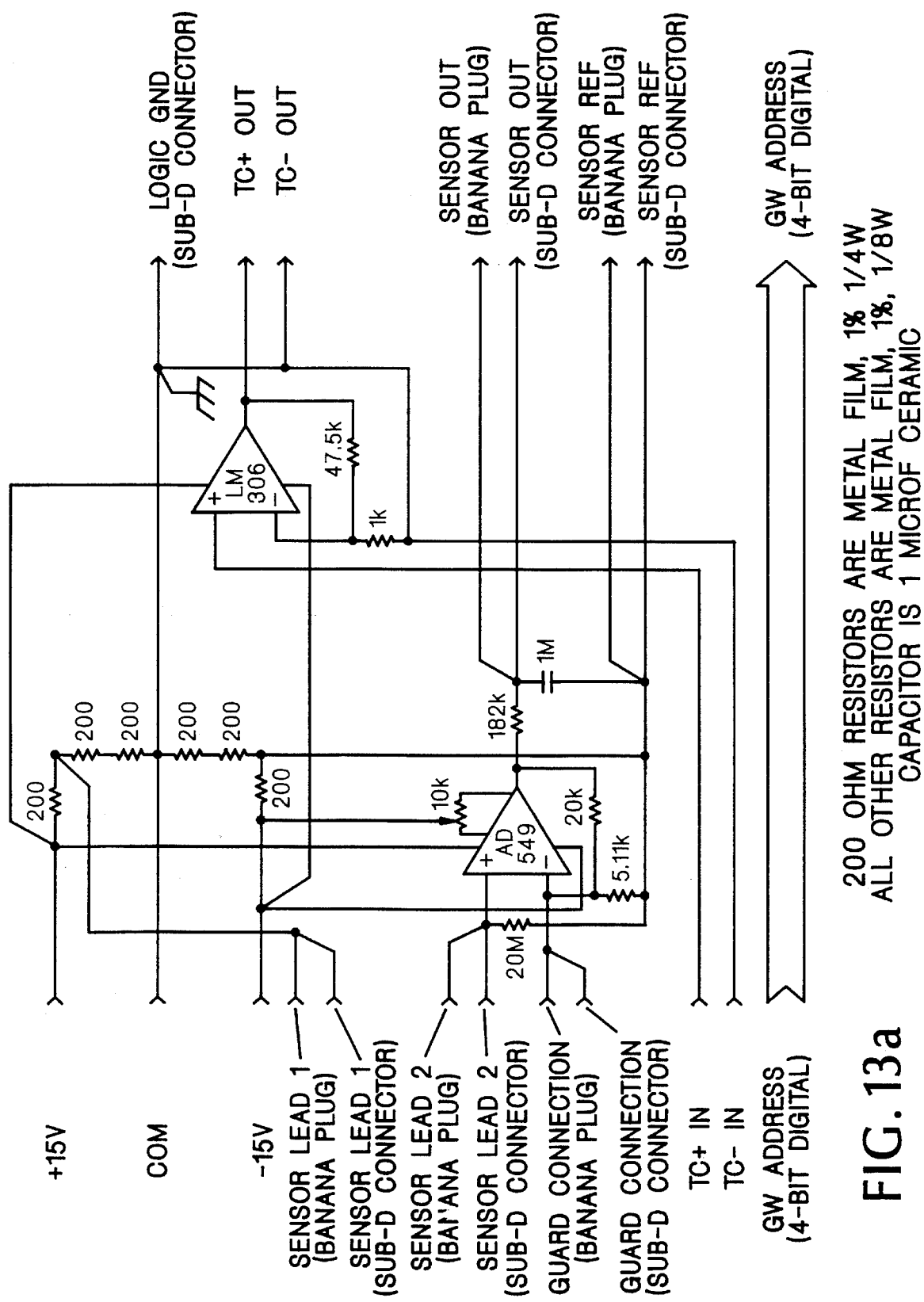

Referring to FIG. 13a, the Main Interface Unit (MIU) is used to convert the resistance change in the resin into voltage variation for the computer with the resin modelled as a variable resistor in one leg of the bridge. The measured resistance varied over a range of 10 to $10^6$ MΩ; thus, with a 10 V input potential, the current varied between 0.1 µA to 0.01 nA. The small current resulting from the large resin resistance increased the system sensitivity to noise. In order to prevent this current signal from being corrupted by leakage current and aerial noise, precision circuit design practices in developing the MIU and associated electronics can be used, including: (1) using low-bias, high stability operational amplifiers (op-amps); (2) using proper guarding, grounding and shielding practices; (3) properly isolating the op-amps to assure that they do not load each other; (4) using low-pass filters; (5) using high precision resistors and capacitors in the signal path; and (6) using an aluminum enclosure. Such design practices are well-known to those of skill in the art and are described in Horowitz and Hill, The Art of Electronics, 2nd Ed. Cambridge University Press, N.Y. 1990, Chapter 7. All circuits were built on a fiberglass circuit board with connections prepared by wire-wrapping and soldering with all chips being inserted into either plastic or Teflon sockets. All circuit boards were mounted inside aluminum enclosures and stood on ceramic standoffs and external connections were provided through banana plugs and D-subminiature connectors.

The circuitry inside the MIU is in five parts: (1) voltage reducer, (2) signal bridge, (3) sensor signal amplifier, (4) low-pass filter, and (5) secondary thermocouple amplifier.

Figure 13B:
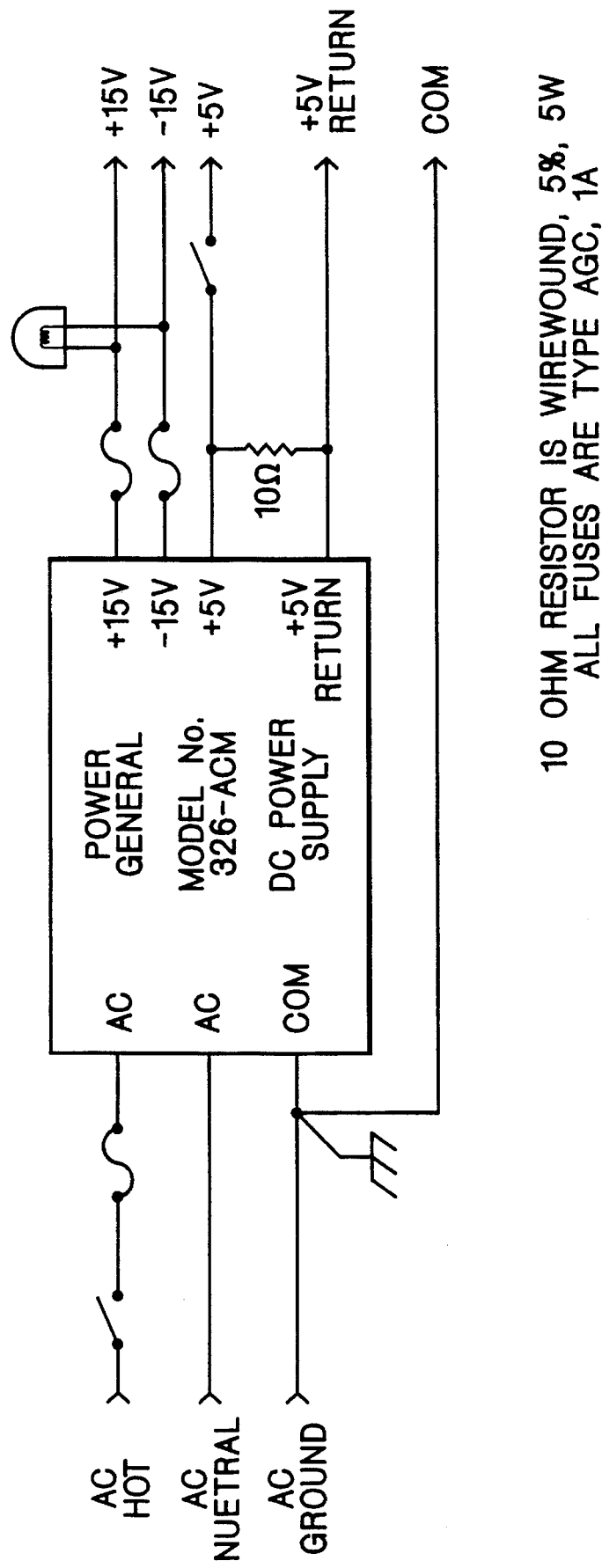

Referring to FIG. 13b, a 30 V DC potential was used to provide electrical power to the MIU circuitry with a dedicated power supply, for example, a Power General ADC369 DC Power Supply (Power General, Canton, Mass.) having a ±15 V output rated at 0.4 A and a +5 V output rated at 2A. The ±15 V supply is directed to the op-amp supplies and to the voltage reducer of the MIU. The voltage reducer reduces the ±15 V input to +10 V before being supplied to the rest of the circuit in order to avoid operating the op-amp near its supply voltage, where the op-amps exhibit nonlinear behavior.

The ±10 V DC potential is applied via the signal bridge across the resin and a fixed 20 MΩ resistor to keep the voltage measured across the fixed resistor above 1 V at viscosity minimum. This is determined experimentally with the particular resin. All measurements are taken with respect to the −10 V potential at the lower end of the bridge with the ground floating. The fixed resistor, as well as other resistors in the signal path are selected to be 1% metal film resistors.

Referring again to FIG. 13a, the output of the signal bridge is fed into a low-bias op-amp (Analog Devices Model 549, Norwood, Mass.) used as a fixed-gain amplifier. The low-bias amplifier increases the amplitude of the signal and buffers the high output resistance of the bridge. The op-amp is inserted into a Teflon socket to minimize leakage. The amplifier has a gain between 2–5 to maximize the voltage output to the computer which is varied by changing the ratio of the feedback resistors.

In order to improve rejection of airborne AC noise, especially the 60 Hz interference from power lines, a low-pass filter is provided at the output of the amplifier. The low-pass filter is a simple RC circuit with a 162kΩ resistor and a 1 µF ceramic capacitor to yield a cutoff frequency at approximately 1 Hz.

The other section of the MIU is a secondary thermocouple amplifier circuit including a general purpose op-amp, National Semiconductor LM340, Santa Clara, Calif., which serves to increase the input signal from a thermocouple reader to a voltage range between 0–10 V. The outboard thermocouple reader is an Omega Engineering Model TAC386JC, Stamford, Conn., compatible with a type J thermocouple. The output from the thermocouple reader is 1 mV per degree Celsius with the accuracy being +1 degree. Because measurements below 200° C. are needed, a gain of 48.5 is used.

Figure 13C:
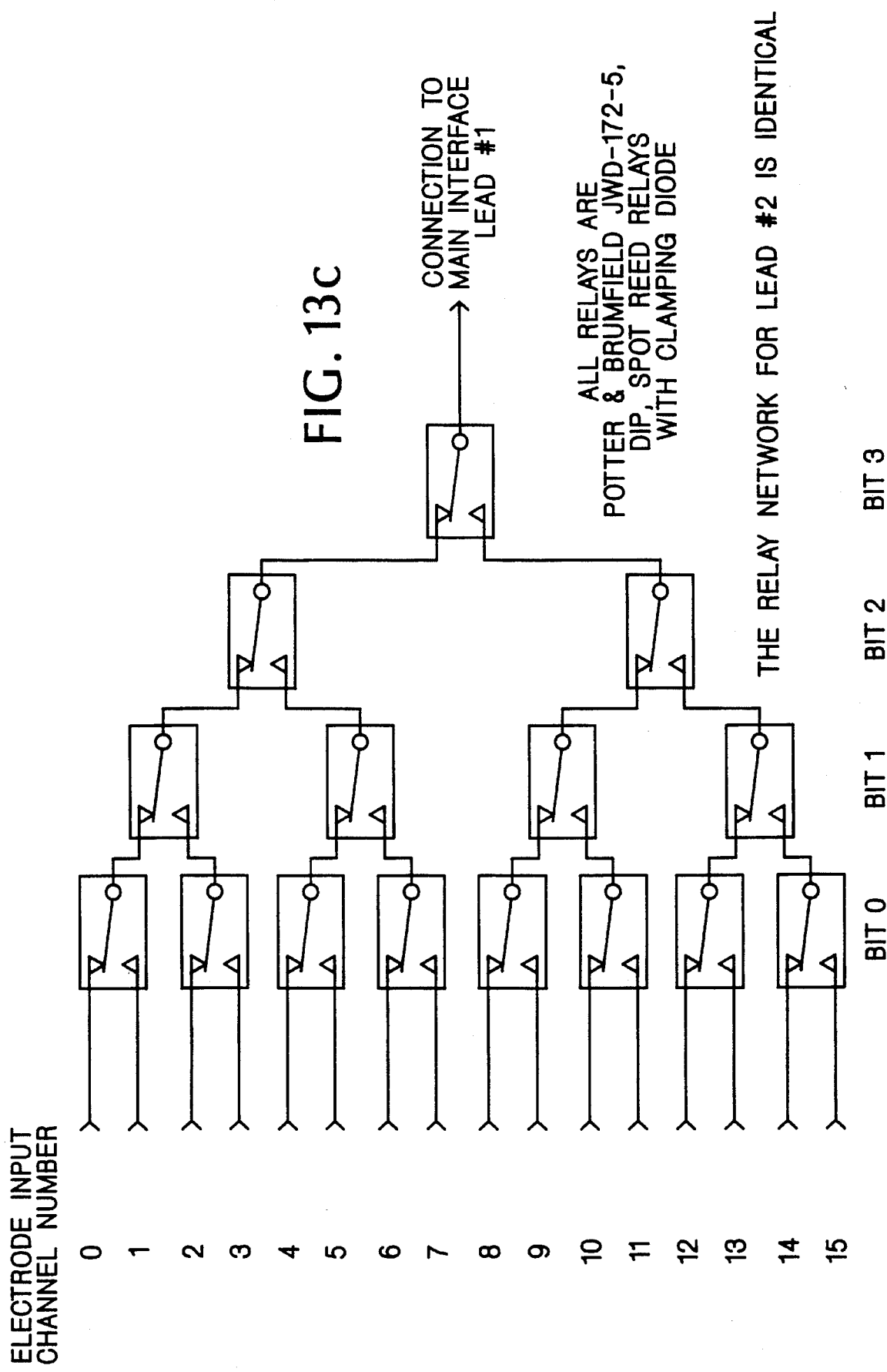
Figure 13D:
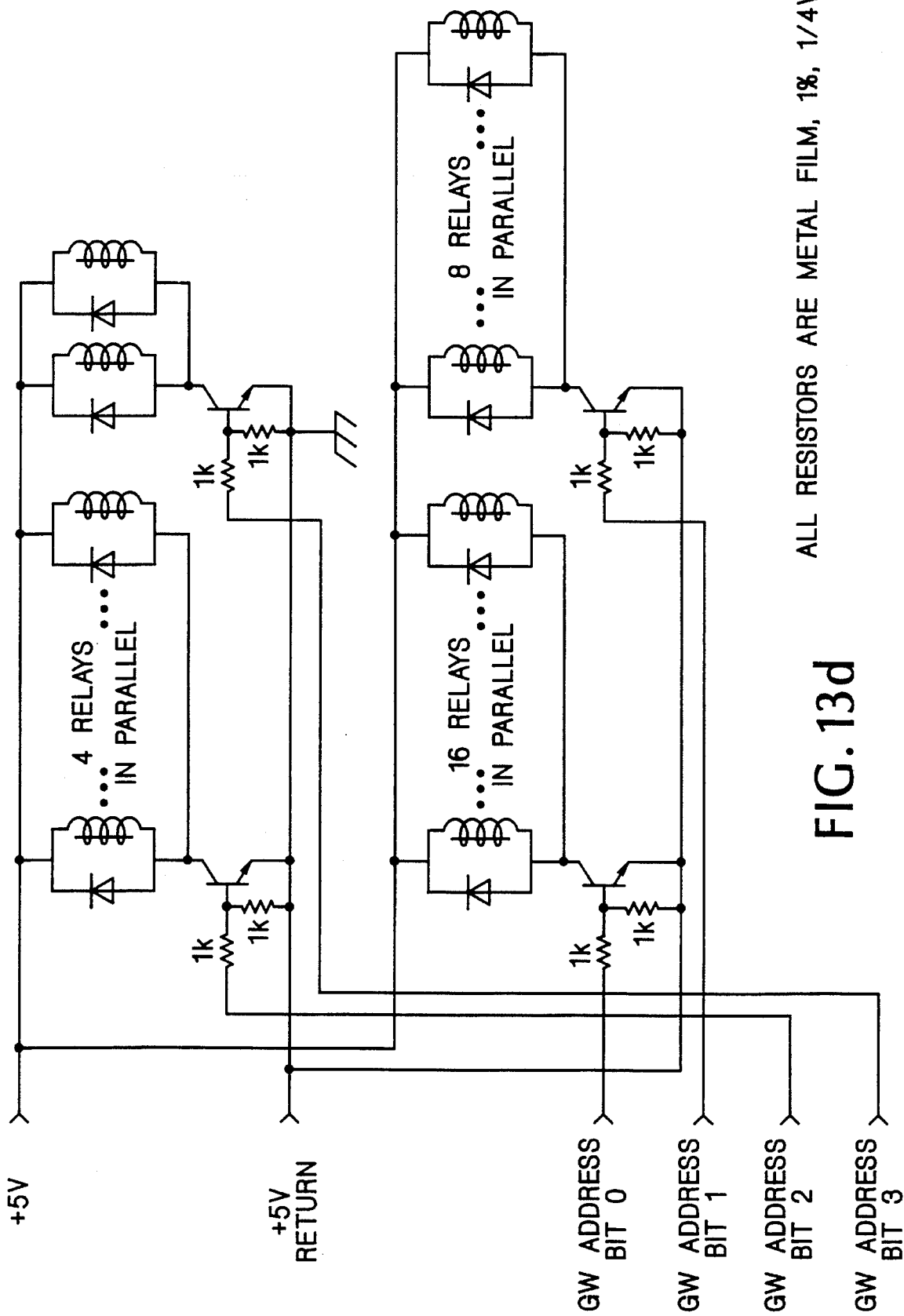

Referring to FIG. 13c, the signal is multiplexed while it is still in the analog domain. In order to maintain signal quality through the multiplexer, a network of relays is provided. (Other multiplexer electronics are possible, for example dedicated amplifier circuits for each channel or a digital multiplexer.) The signal path in the multiplexer is laid out in a tree-structure network. In this embodiment, the 4-bit digital word size of the DAS16 A/D board limited the tree to 4 layer and 16 channels. Fifteen dry Reed switch relays were used for each tree and two identical trees are provided for the electrode pair. The relays are 5 V, single-pole, double-throw relays (Model JWD-172-5 from Potter and Brumfields Electronics, Princeton, Ind. Referring to FIG. 11d, a current switch including npn transistors (National Semiconductor Model 2N2222) were used to switch each layer of relays (each layer being 1 bit).

In order to improve noise rejection, special attention is paid to shielding, guarding, and grounding of the electronics. Coaxial cable was used for all signal connections between the computer and the MIU, the MIU and the multiplexer, and the multiplexer and the electrodes. In the first two cases, the shields are connected to the aluminum enclosures and to the A/D board's power ground. Because the computer and the Data General power supply (Model ADC369) are plugged into separate wall outlets, a ground connection is not established between the power supply and the MIU to avoid a ground loop.

Ideally, the entire signal path from the point of measurement to the amplifier input should be guarded to eliminate leakage paths. For printed circuit boards, guarding can be implemented by printing a ring around the signal path. The use of coaxial wire is generally effective in providing guarding for wires either wire-wrapped or soldered to the circuit. Guarding was not done inside the MIU, nor the multiplexer. The only segment of the signal path that is guarded is between the multiplexer and the electrode connection. Coaxial cable is used in this segment of the signal path with the outer coaxial jacket serving as the guard. The guard is hardwired through the multiplexer and back to the MIU, and terminated at the inverted input of the op-amp. Ideally this guard should continue into the electrode and into the rest of the electronics. As discussed earlier, the exposed carbon fibers at the end of each electrode are sandwiched between copper tapes. The electrodes are connected to the multiplexer by clamping the copper tape in a spring-load contact. This is the point where the guard in the coaxial cable ends. The guard could be extended to the point of measurement using designed contact and coaxial electrodes.

Figure 13E:
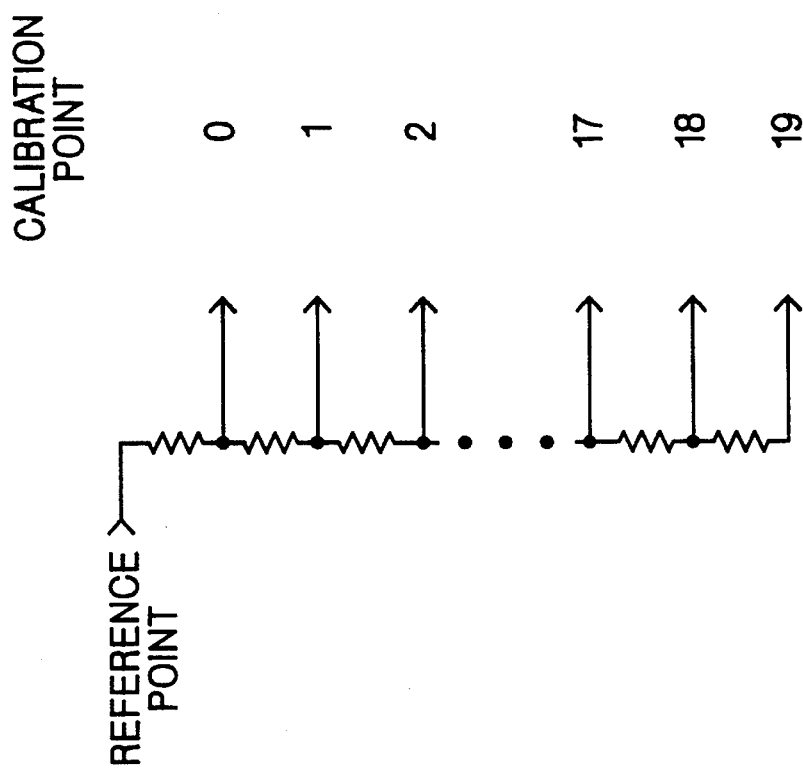

Referring to FIG. 13e, in order to determine the accuracy of the circuit and the noise level in the circuit, a resistor array was built with fifty 20 MΩ, 5% resistors linked in series to provide a calibration range of 20 to $10^3$ MΩ. Eighteen different points in the resistor chain are tapped for measurement. The step size was 20 MΩ for the first 10 points and 100 MΩ for the next 8 points. Measurements were zeroed with a potentiometer in the amplifier circuit.

The error between the measured and the actual resistance is initially below 1% with a steady increase towards 2.5%, and indications that the error decreases thereafter. Two factors account for the increase in noise level as the resistance increased, including 1) ambient noise and 2) quantization error. The ambient noise the signal picks up as it travelled from the calibration resistor array to the computer is relatively constant throughout a given measurement session. Therefore, as the resistance increases (i.e. voltage in the transmission line decreases), the same noise becomes increasingly dominating. Moreover, as the voltage drops to low levels, the D/A board's quantization error becomes increasingly significant. The accuracy for the DAS 16 was 0.01% ±1LSB, which translated into an accuracy of 0.63% at 1000M, with quantization error accounting for 0.62% of the 0.63% accuracy value.

If the ambient noise and quantization error are modeled as a constant voltage error, V, then:

$$V_{MEASURED} = V_{ACTUAL} + \Delta V$$

or expressed in terms of resistance difference, $$\Delta R = R_{MEASURED} - R_{ACTUAL} =$$

$$R_{FIXED} V_S \left( \frac{1}{V_{ACTUAL} + \Delta v} - \frac{1}{V_{ACTUAL}} \right)$$

Where $V_s$ is the input potential to the bridge. The absolute percentage error, $(\Delta R/R_{ACTUAL}) \times 100$, was simulated for a scenario in which $V_s = 20$ V, $R_{FIXED} = 20$ MΩ, and at two different errors, one at +3 mV and one at −3 mV. When the error is additive, the resistance error increases slowly and reaches the 50% mark when the voltage input is at the noise level of 3 mV, and the 55% mark when the input was at the LSB level of 2.44 mV. When the error is subtractive, the resistance error shoots up quickly to slightly over 100% and is clipped by the LSB limit at that point. The error is generally additive. The performance of the sensor is relatively insensitive to this error. This was believed to be due to: (1) the magnitude of resistance variation during curing of the resin being very large, and dominated over the noise, (2) the amplitude of the resistance being generally not important, but rather the shape of the curve being significant, and the shape of the curve not sensitive to a constant error, (3) the A/D board being very consistent, so bit fluctuation due to quantization error is relatively infrequent.

Test Conditions

A test cell was constructed to make measurements for the resin sample. The cell is milled from a solid block of aluminum. The cell has three parts, a top plate, a base, and a cover. The top plate measured 3" by 5" by 0.375" with a 1.5" by 2.5" by 0.2" cavity in the center for holding the test sample. Two 0.2" by 0.2" channels run into the cavity from the two shorter sides. Sensors and thermocouples enter the cavity through these channels. Vacuum tape is used to seal off the rest of the channel volume not occupied by the sensor, to prevent the resin from leaking out of the test cell.

A hole is drilled in the center of the cavity, through the base, to accommodate a 1" microdielectrometer Tool-Mount Sensor (TMS), from Micromet Instruments, Inc., Newton, Mass. (Note: The extra length in the base allows the steel sheath of the TMS cable to make a 90° turn and exit horizontally, so the test cell can be placed in a press. The electrode spacing on the 1" TMS is 0.075". Since the fringe field penetration depth of the TMS is about the same as its electrode spacing, the test cavity is at least as deep as the electrode spacing.) A flat piece of 0.0625" aluminum cover sits above the top plate during all experiments to improve heat conduction and squeeze out excess resin. The test cell is electrically grounded to the enclosures for the electronics.

In the measurements, the sensors and a J-type thermocouple enter the cavity through the side channels. Vacuum tape is used to seal off the channels and secure the sensors. A sheet of Teflon film is placed on the bottom of the cavity to protect the TMS and to eliminate any possible conduction path between the exposed tip of the sensors and the aluminum mold. Perforations are made in the Teflon film in the area just above the TMS. This allows the TMS to gain contact with the resin, while keeping the carbon reinforcing fibers away. The Teflon film is also used in experiments with resin alone to ensure identical experimental set-up. The ends of the sensors is typically spaced about 0.4 inch (1 cm) apart, located right over the TMS, but separated by the Teflon film. The test cell is used in a Tetrahedron pneumatic press programmed for zero compression force. Teflon film is used to cover the top and bottom heating plates. The film is used to electrically decouple the mold from the press and to facilitate clean-up. All cure cycles are isothermal. The ramp rate is set at around 5° C. per minute with the cure temperatures being typically 177° C. and 191° C. However, in order to maintain the desired temperature inside the rather large test cell, the tool temperature was set another 2.8° higher than the intended cure temperature. The TMS is used in conjunction with a thermoset testing system (for example, ICAM-1200 system, a product of Micromet Instruments, Inc., Newton, Mass.) for making measurements at a frequency of 100 hertz.

One thermoset resin used in the experiments is PR 500 epoxy (Lot 102 KO2 and Lot 205 G1A, 3M, Aerospace Materials Department, Minneapolis, Minn.). The resin is a solid at just below room temperature and has a low viscosity, at viscosity minimum, about 0.6–0.7 poise. Two batches of the resin were available. Another thermoset resin which may be used is *1919* epoxy (Hercules Advanced Materials and Systems, Composite Products Group, Magna, Utah. The resin is used in the form of a prepreg tape with the tape being an unidirectional carbon fiber tape having a thickness of approximately 0.77 inch.

Data

Figure 14:
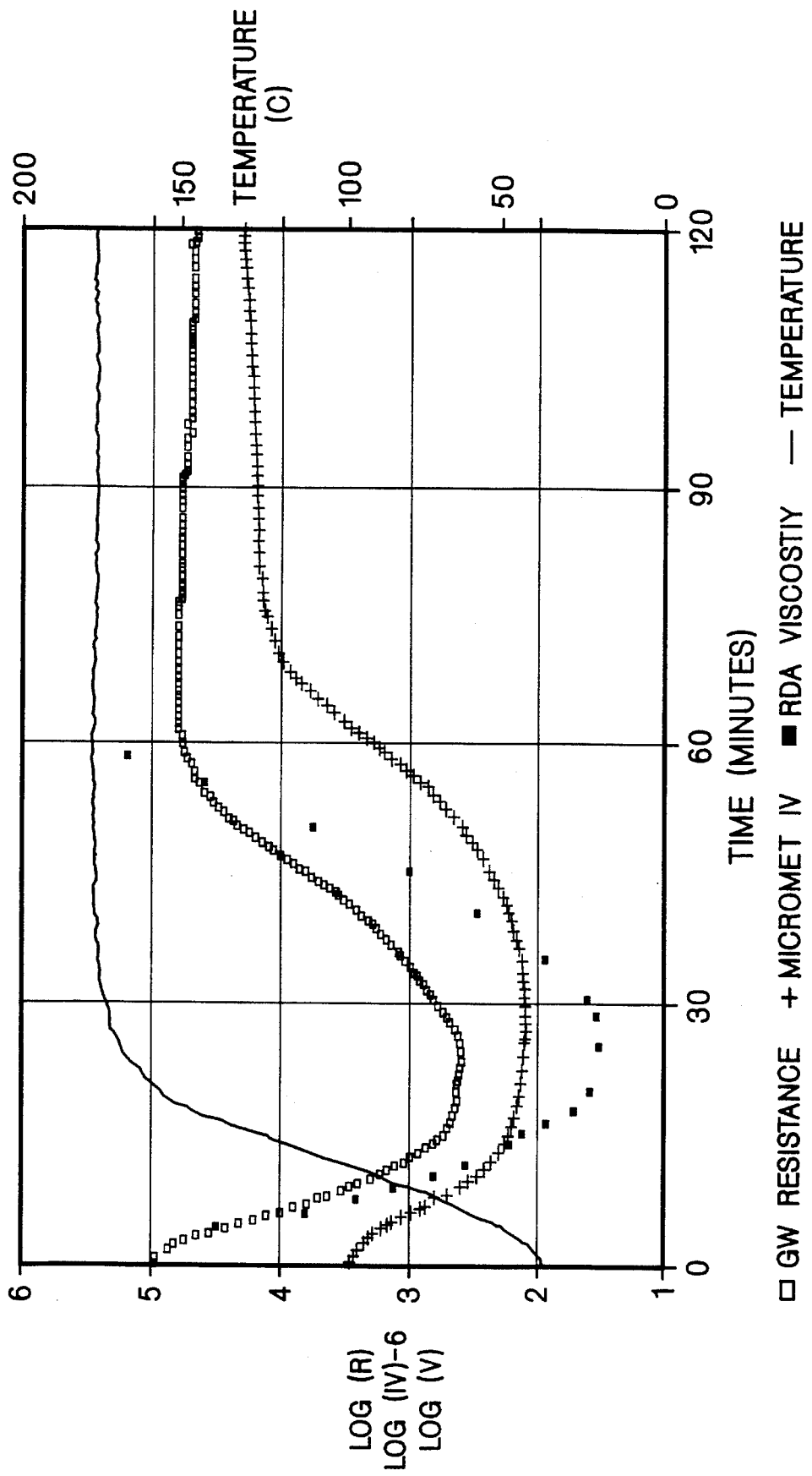
FIGS. 14 and 14a are ion viscosity versus time graphs determined by a sensor according to the invention.
Figure 14A:
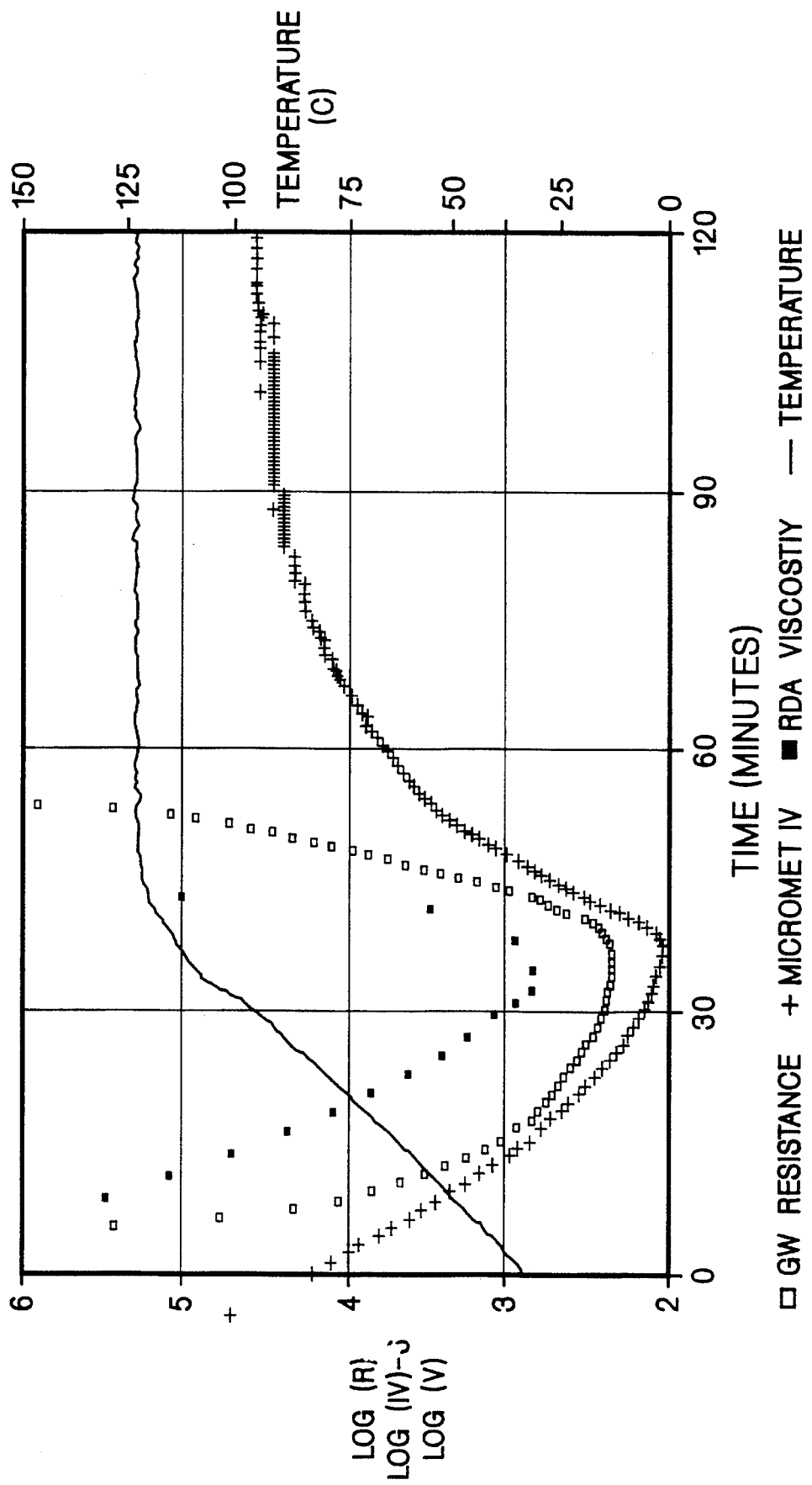

The cure measurement capability of the sensor is summarized in FIGS. 14 and 14a. Referring to FIG. 14 the signal from the sensor is plotted against the ion viscosity data measured with the microdielectric TMS, as well as the manufacturer supplied viscosity data for the resin (PR-500 resin from 3M). It is evident that viscosity minimum and end of cure can be identified by the sensor. The gel point appears slightly different for the sensor and the TMS. The dielectric trace shows the gel point in the maximum slope region. The sensor trace shows gel point in the sudden "slow down" (signal leveling off) region.

Referring to FIG. 12a the signal from the sensor is plotted against the ion viscosity data measured with the microdielectric TMS, as well as the manufacturer supplied viscosity data for the prepregnated resin (Hercules 1919). Identification of viscosity minimum in this case is straight forward as before. Identification of end of cure is not possible with the sensor in this case, because the DC resistance became very large after gelation. The dielectric trace shows the gel point at the maximum slope region. The sensor trace shows gel point at the sudden "slow down" (a decrease in slope) region.

The cure sensor should be calibrated for each resin. The correlation between critical points on the sensor output and rheometric viscosity will be generally the same as discussed above, with some slight differences from resin to resin. While the detection of viscosity minimum is always available and gel region requires calibration, end of cure is not always detectable. However, most system dynamics take place before gel inflection. End of cure can simply be timed from either viscosity minimum or gel inflection.

Experiments were also performed with 3K 7H satin weave carbon and glass fabrics and PR500 resin. The fabrics were 2.25 inch by 1.25 inch in size. Eight plys of fabrics and two sheets of solid resin were stacked on top of the sensor and TMS. One sheet of resin was in between the sensor and the bottommost sheet of fabric, and the other sheet of resin was positioned between the fourth and fifth ply of fabric. The fiber volume was between 30 to 40 percent. The presence of the fibers did not substantially effect the cure or measurement by the sensors.

Figure 15:
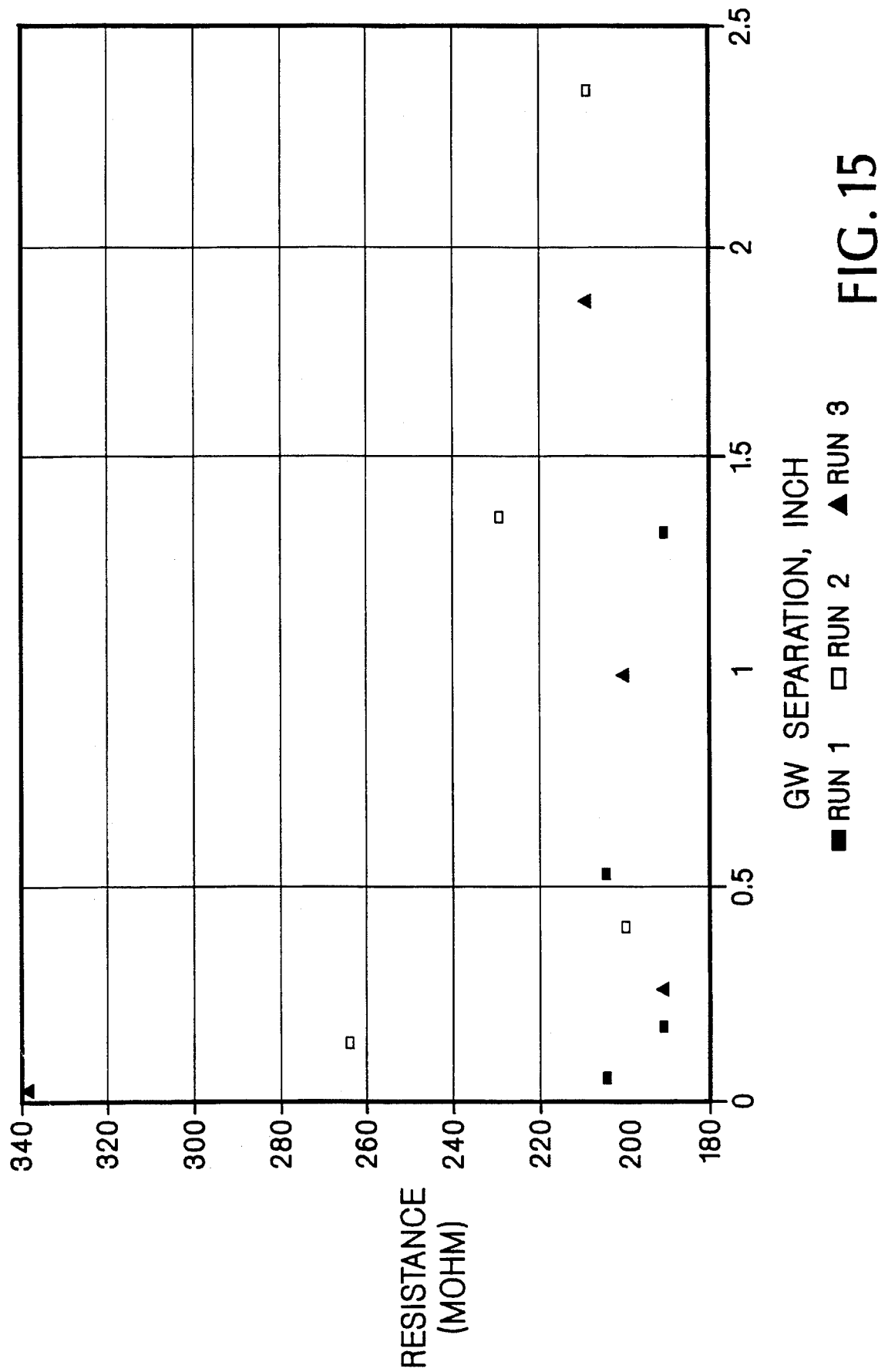
FIG. 15 is a graph of resistance versus gap size for a sensor according to the invention.

As mentioned, the resistance measurement made with the sensors do not vary greatly with gap width. Referring to FIG. 15, the resistance is plotted as a function of different gap width. Tow size, polymer coating, coating thickness, and resin were the same as described above. Three sets of measurements were made with four sensors of different gap widths disposed in the test cell and measurement from each sensor made sequentially. As the data shows, the resistance in a typical case did not vary substantially (within about 40 megaohms) with gap width over a range of about 0.1 inch to 2.25 inch. The variation in resistance is particularly small in view of the resistance variation over a cure cycle, which is typically three orders of magnitude.

What is claimed is:

1. A sensor for measuring the properties of a resinous material, comprising:

a pair of thread-like members each being composed of an electrically conductive strand having preformed insulating material over its length and extending to an end at which said conductive material is exposed, said exposed conductive material non-protruding from said insulating material, said ends of said thread-like members being spaced to form a sensing gap where a property of said resinous material in said sensing gap is measured by connecting said strands to sensor electronics that are located remotely from said sensing gap.

2. The sensor of claim 1 wherein said ends of said strands are spaced and arranged to form an axial gap.

3. The sensor of claim 1 wherein said sensor is constructed for measuring the properties of a composite material composed of resin and conducting components, the ends of said strands being spaced a distance less than the width of said conducting components.

4. The sensor of any one of claims 1 to 2 wherein said ends of said strands are spaced between about 0.01 to 2.25 inches.

5. The sensor of claim 1 wherein said strands have a diameter in the range of 100 µm to 2 mm.

6. The sensor of claim 1 wherein said sensor is constructed for measuring the properties of a composite material composed of resin and conducting reinforcing fibers, and said conductive strands being composed of the same substance as said reinforcing fibers.

7. The sensor of claim 6 wherein said conductive strands and said reinforcing fibers have comparable cross-sectional dimensions.

8. The sensor of claim 6 or 7 wherein said conductive strands and reinforcing fibers are composed of carbon fibers.

9. The sensor of claim 1 wherein said insulating member is a coating that bonds to said resinous material.

10. The sensor of claim 9 wherein said polymer coating is formed from a resin that is in a partially cured state prior to placing said sensor in contact with said resinous material, said resin forming said polymer coating being cured under conditions that cure the resin of said resinous material.

11. The sensor of claim 9 or 10 wherein said insulating polymer coating is formed from the same resin used in said resinous material.

12. The sensor of claim 1 wherein said insulating member incorporates a glass fiber sock and an insulating polymeric material.

13. The sensor of any one of claims 2 wherein said space between said ends includes a substance with an electrical property that varies with said material property.

14. The sensor of claim 14 wherein said substance is a pressure-sensitive polymer with an electrical property that varies with pressure applied to the polymer.

15. The sensor of claim 14 wherein said substance is a temperature-sensitive polymer with an electrical property that varies with the temperature of the polymer.

16. The sensor of claim 1 wherein said property is a DC electrical property.

17. The sensor of claim 16 wherein said DC electrical property is an electrical resistance of the resinous material.

18. The sensor of claim 16 wherein said DC electrical property is a complex dielectric property of the resinous material.

19. A system for measuring the properties of a composite material comprising resin and reinforcing fibers, said system, comprising:

a sensor positioned in contact with said resin, said sensor having a pair of thread-like members, each composed of an electrically conductive strand having a preformed insulating material and small regions of exposed conductor, free of said insulating material, said thread-like members arranged to space said exposed regions to form a sensing gap where a property of said composite material is measured, and sensor electronics connected to said strands for measuring said property.

20. The system of claim 19 comprising:

a plurality of said sensors arranged with said sensing gaps at desired positions across said resinous material, said sensor electronics for monitoring cure properties of said resinous material from said sensing gaps.

21. The system of claim 20 wherein said composite material including said resin and reinforcing fibers is formed as a fabric or mat, and said thread-like members are integrated in the reinforcing fabric or mat.

22. The system of claim 21 wherein said sensing gap is formed by the ends of said conductive strands being axially opposed.

23. The system of claim 22 wherein said thread-like members are arranged in multiple layers forming a grid pattern, said sensing gaps formed at overlapping regions of threads in different layers.

24. The system of claim 19 wherein said sensor and sensor electronics are constructed to measure the presence of resin at the sensing gap.

25. The system of claim 19 herein said sensor and sensor electronics are constructed to measure the degree of cure of the location of said sensor.

26. The system of claim 19 wherein said sensor and sensor electronics are constructed for measuring properties of said material after cure of said material.

27. The system of claim 19 wherein said property is a DC electrical property.

28. An article of manufacture comprising:

a cured composite comprised of a resin, including embedded therein, a sensor having at least a pair of thread-like members, each composed of a carbon fiber with a preformed insulating polymer, and small exposed regions of said carbon fiber, free of said insulating polymer, said thread-like members arranged to space said exposed regions to form a sensing gap, where a property of said composite is measured by connecting said sensor to sensor electronics located remotely from said composite.

29. The article of manufacture of claim 28 wherein said property is a DC electrical property.

30. The article of manufacture of claim 28 wherein said cured composite further comprises conductive reinforcing fibers and said small exposed regions of said carbon fibers are sized less than the diameters of the reinforcing fibers.

31. A sensor for measuring multiple properties of a composite material comprising resin and reinforcing fibers, said sensor comprising:

a pair of thread-like members composed of a pair of electrically conductive strands, each having preformed insulating material and a region free of said insulating material, said thread-like members arranged to space said regions to form a sensing location, said sensing location including a property sensitive material different from said resin, said strands being constructed for connection to sensor electronics.

32. The sensor of claim 31 wherein said conductive strands are arranged concentrically.

33. The sensor of claim 31 wherein said conductive strands are arranged in parallel.

34. The sensor of claim 31 wherein said conductive strands are arranged to be exposed to said composite material in said sensing location for measuring a first material property, and said conductive strands are arranged to be exposed to a polymeric substance with an electrical property that varies with a second material property.

35. The sensor of claim 31 wherein said polymeric substance is selected from the group consisting of temperature-sensitive polymers and pressure sensitive polymers.

36. The sensor of claim 31 further comprising a plurality of sensing locations defined by exposed regions of said conductive strands, free of said insulating material.

37. The sensor of claim 36 wherein one of said sensing locations is defined by electrically conductive strands having said insulating material extending to ends at which said conductive material is exposed, flush with said insulating material, said ends of said strands spaced to form one of said sensing locations having property sensitive material disposed between said ends of said strands.

38. The sensor of claim 31 wherein said property is a DC electrical property.

39. The sensor of claim 31 wherein said sensor electronics comprise a DC bridge network.

40. A system for measuring the properties of a composite material comprising resin and reinforcing fibers, said system, comprising:

a sensor positioned in contact with said resin, said sensor having a pair of thread-like members each being composed of an electrically conductive strand having preformed insulating material over its length and extending to an end at which said conductive material is exposed, said exposed conductive material non-protruding from said insulating material, said ends of said thread-like members being spaced to form a sensing gap where a DC electrical property of said resinous material in said sensing gap is measured; and sensor electronics connected to said strands for measuring said DC electrical property.

* * * * *

UNITED STATES PATENT AND TRADEMARK OFFICE
CERTIFICATE OF CORRECTION

PATENT NO. : 5,528,155
DATED : June 18, 1996
INVENTOR(S) : King, et al.

Page 1 of 2

It is certified that error appears in the above-identified patent and that said Letters Patent is hereby corrected as shown below:

On the title page item [56],

References are missing from Other Publications section:

Please insert the following references:

--Micromet Instruments, Inc., Cambridge, Massachusetts, "Cure Monitoring" product literature--

--Shepard, D., "Dielectric Device Cure Monitoring Goes Micro," Micromet Instruments, Inc., Cambridge, Massachusetts--

Sheet 10 of 16, Fig 13b, replace "NUETRAL" with --NEUTRAL--

UNITED STATES PATENT AND TRADEMARK OFFICE
CERTIFICATE OF CORRECTION

PATENT NO. : 5,528,155

DATED : June 18, 1996

INVENTOR(S) : King, et al.

It is certified that error appears in the above-identified patent and that said Letters Patent is hereby corrected as shown below:

Col. 6, line 3, delete "$\mu$"

Col. 6, line 33, replace "composite" with --composite. The--

Col. 17, line 28, replace "claims" with --claims 1 or--

Col. 17, line 31, replace "14" with --13--

Col 17, line 34, replace "14" with --13--

Col. 18, line 4, replace "22" with --20--

Col 18, line 11, replace "herein" with --wherein--

Col. 19, line 5, replace "31" with --38--

Signed and Sealed this

Sixth Day of January, 1998

BRUCE LEHMAN

Attest:

*Attesting Officer*  *Commissioner of Patents and Trademarks*